US011944343B2

(12) United States Patent
Jalgaonkar et al.

(10) Patent No.: US 11,944,343 B2
(45) Date of Patent: Apr. 2, 2024

(54) ASPIRATION CATHETER INCLUDING MECHANICAL CUTTER

(71) Applicant: Covidien LP, Mansfield, MA (US)

(72) Inventors: Ujwal Jalgaonkar, Irvine, CA (US); Syamala Rani Pulugurtha, Irvine, CA (US)

(73) Assignee: Covidien LP, Mansfield, MA (US)

( * ) Notice: Subject to any disclaimer, the term of this patent is extended or adjusted under 35 U.S.C. 154(b) by 239 days.

(21) Appl. No.: 17/308,830

(22) Filed: May 5, 2021

(65) Prior Publication Data

US 2022/0354528 A1   Nov. 10, 2022

(51) Int. Cl.
*A61B 17/3207* (2006.01)
*A61B 17/00* (2006.01)
*A61B 17/32* (2006.01)
*A61B 90/00* (2016.01)

(52) U.S. Cl.
CPC ............. *A61B 17/32075* (2013.01); *A61B 2017/00557* (2013.01); *A61B 2017/320012* (2013.01); *A61B 2017/320064* (2013.01); *A61B 2090/034* (2016.02); *A61B 2090/08021* (2016.02); *A61B 2217/005* (2013.01)

(58) Field of Classification Search
CPC ........... A61B 2017/320012; A61B 17/320725; A61B 2017/320775; A61B 2017/320064; A61B 17/320758
See application file for complete search history.

(56) References Cited

U.S. PATENT DOCUMENTS

| 5,295,958 A | * | 3/1994 | Shturman | ............ | A61M 60/896 |
| | | | | | 606/159 |
| 5,569,275 A | | 10/1996 | Kotula et al. | | |
| 5,882,329 A | * | 3/1999 | Patterson | ............ | A61B 17/3207 |
| | | | | | 604/523 |

(Continued)

FOREIGN PATENT DOCUMENTS

| CN | 110393575 | 11/2019 |
| DE | 2933266 A1 | 5/1981 |

(Continued)

OTHER PUBLICATIONS

Extended Search Report from counterpart European Application No. 22163436.3 dated Sep. 12, 2022, 12 pp.

*Primary Examiner* — Kathleen S Holwerda
*Assistant Examiner* — Serenity A Miller
(74) *Attorney, Agent, or Firm* — Shumaker & Sieffert, P.A.

(57) ABSTRACT

In some examples, a catheter includes an elongated body defining an inner lumen and comprising an expandable member disposed at a distal portion of the elongated body, and a rotatable cutting tool located within an inner lumen of the elongated body, the rotatable cutting tool configured to segment a thrombus into smaller pieces while an aspiration force pulls the thrombus proximally into the inner lumen. In some examples, the catheter further comprises an intermediate structure oriented radially between the rotatable cutting tool and an interior surface of the elongated body, the intermediate structure configured to prevent the cutting tool from contacting the interior surface of the elongated body. In some examples, a stopper is configured to limit movement of the cutting tool distally past a distal end of the expandable member.

18 Claims, 8 Drawing Sheets

(56) References Cited

U.S. PATENT DOCUMENTS

| | | | |
|---|---|---|---|
| 8,579,926 B2* | 11/2013 | Pintor | A61B 17/320758 |
| | | | 606/159 |
| 9,848,975 B2 | 12/2017 | Hauser | |
| 10,383,691 B2 | 8/2019 | Hendrick et al. | |
| 2007/0250096 A1 | 10/2007 | Yamane et al. | |
| 2008/0004647 A1* | 1/2008 | To | A61B 17/320758 |
| | | | 606/159 |
| 2009/0171368 A1 | 7/2009 | Pearce et al. | |
| 2011/0213297 A1 | 9/2011 | Aklog et al. | |
| 2014/0277015 A1 | 9/2014 | Stinis | |
| 2015/0173782 A1* | 6/2015 | Garrison | A61M 25/0023 |
| | | | 606/127 |
| 2015/0342629 A1 | 12/2015 | Schneider | |
| 2018/0256179 A1* | 9/2018 | Hayakawa | A61B 17/221 |
| 2019/0239905 A1* | 8/2019 | Olson | A61B 17/221 |
| 2019/0269491 A1* | 9/2019 | Jalgaonkar | A61M 25/0067 |
| 2020/0170666 A1 | 6/2020 | Trosper et al. | |
| 2020/0205838 A1 | 7/2020 | Walzman | |
| 2020/0222171 A1 | 7/2020 | Nguyen et al. | |
| 2021/0267613 A1* | 9/2021 | Follmer | A61B 17/221 |
| 2022/0287729 A1* | 9/2022 | Phillips | A61B 17/221 |

FOREIGN PATENT DOCUMENTS

| | | |
|---|---|---|
| DE | 29722136 U1 | 4/1999 |
| EP | 2881047 A1 | 6/2015 |
| WO | 2002019928 A2 | 3/2002 |
| WO | 2019118586 A1 | 6/2019 |
| WO | 2021003133 A1 | 1/2021 |

* cited by examiner

ASPIRATION CATHETER INCLUDING MECHANICAL CUTTER

TECHNICAL FIELD

This disclosure relates to a medical catheter.

BACKGROUND

A medical catheter defining at least one lumen has been proposed for use with various medical procedures. For example, in some cases, a medical catheter may be used to access and treat defects in blood vessels, such as, but not limited to, lesions or occlusions in blood vessels.

SUMMARY

This disclosure describes example catheters including a mechanical cutting tool (or "cutter") configured to segment a thrombus, which is aspirated into an inner lumen of the catheter, into smaller pieces. The catheter may include an elongated body and an expandable member at a distal portion of the elongated body and defining at least part of a distal tip of the catheter. The expandable member is configured to expand radially outward within a hollow anatomical structure (e.g., a blood vessel) of a patient, e.g., to engage a thrombus. In some examples, the mechanical cutting tool is configured to segment the thrombus as an aspiration force pulls the thrombus proximally into an inner lumen of the elongated body. For example, the mechanical cutting tool can be introduced into the inner lumen of the elongated body and positioned within, or at least partially proximal to, the expandable member. In response to a continuous or varying aspiration force, a distal mouth of the expandable member envelops and engages a portion of the thrombus and the mechanical cutter engages and segments the thrombus into smaller pieces to facilitate efficient aspiration through the elongated body.

In some examples, the mechanical cutter includes a plurality of bristle-like extensions projecting radially outward from a support member. The extensions are configured to rotate about a rotational axis to segment (e.g., cut) the thrombus. As described herein, the mechanical cutter (or a medical system including the catheter) may include any of a number of additional features, including, but not limited to, an intermediate feature configured to modulate a radial position of the cutter within the inner lumen of the catheter, a stopper configured to modulate an axial position of the cutter within the inner lumen of the catheter, or a distal element configured to mechanically compress the thrombus into the inner lumen of the catheter for segmentation. This disclosure also describes examples of methods of forming the catheters described herein and methods of using the catheters.

Clause 1: In some examples, a medical device includes an elongated body comprising an expandable member disposed at a distal portion of the elongated body, the elongated body further comprising an interior surface defining an inner lumen; a rotatable cutting tool located within the inner lumen of the elongated body, the rotatable cutting tool configured to segment a thrombus into smaller pieces while an aspiration force pulls the thrombus proximally into the inner lumen; and an intermediate structure oriented radially between the rotatable cutting tool and the interior surface of the elongated body, the intermediate structure configured to prevent the cutting tool from contacting the interior surface of the elongated body.

Clause 2: In some examples of the medical device of clause 1, the intermediate structure is configured to retain the cutting tool in an approximately radially central position within the inner lumen.

Clause 3: In some examples of the medical device of clause 1 or clause 2, the cutting tool is configured to expand radially outward from a delivery configuration to a deployed configuration, and wherein the cutting tool is configured to rotate within a volume defined by the inner lumen.

Clause 4: In some examples of the medical device of clause 3, while the cutting tool is in the deployed configuration, the cutting tool is radially inwardly compressible.

Clause 5: In some examples of the medical device of any of clauses 1-4, the cutting tool comprises a brush including a plurality of bristles extending radially outward from an elongated support member.

Clause 6: In some examples of the medical device of clause 5, the bristles are substantially rigid.

Clause 7: In some examples of the medical device of clause 5 or clause 6, the brush tapers radially inwardly as it extends in a distal direction.

Clause 8: In some examples of the medical device of any of clauses 1-7, the intermediate structure comprises a sheath that radially surrounds the cutting tool.

Clause 9: In some examples of the medical device of any of clauses 1-8, the medical device further includes a stopper configured to limit movement of the cutting tool distally past a distal end of the expandable member.

Clause 10: In some examples of the medical device of clause 9, the stopper comprises a silicone plug disposed on the cutting tool.

Clause 11: In some examples of the medical device of clause 9 or clause 10, the stopper comprises a fluid-expandable balloon.

Clause 12: In some examples of the medical device of clause 9 or clause 10, the stopper is configured to engage with a lip extending radially inward from the interior surface of the elongated body.

Clause 13: In some examples of the medical device of any of clauses 1-12, the cutting tool is configured to self-expand.

Clause 14: In some examples of the medical device of any of clauses 1-13, the medical device further includes a distal member configured to apply a proximal force onto a distal side of the thrombus to push the thrombus into the expandable member.

Clause 15: In some examples of the medical device of clause 14, the distal member is configured to proximally compress the thrombus against a distal mouth of the expandable member in order to form a fluid-tight seal between the thrombus and the distal mouth to strengthen an effect of the aspiration force on the thrombus.

Clause 16: In some examples of the medical device of clause 14 or clause 15, the distal member is coupled to an elongated support member of the cutting tool.

Clause 17: In some examples of the medical device of any of clauses 14-16, the distal member is proximally and distally movable with respect to the cutting tool.

Clause 18: In some examples of the medical device of any of clauses 14-17, the distal member is configured to expand radially outward from a delivery configuration to a deployed configuration.

Clause 19: In some examples of the medical device of any of clauses 1-18, the cutting tool includes: an elongated support element; and a plurality of radial extensions hingeably coupled to the elongated support element.

Clause 20: In some examples of the medical device of clause 19, the radial extensions are configured to pivot radially outward.

Clause 21: In some examples of the medical device of clause 19 or clause 20, the plurality of radial extensions form an inverted-dome or evergreen-tree shape.

Clause 22: In some examples of the medical device of any of clauses 1-21, the elongated body comprises a catheter.

Clause 23: In some examples of the medical device of clause 22, the expandable member defines an expandable distal mouth of the catheter.

Clause 24: In some examples, a system includes the medical device of claim 1 and an aspiration source configured to generate the aspiration force of claim 1.

Clause 25: In some examples of the system of clause 24, the system further includes control circuitry configured to control a rotation of the cutting tool and configured to control the aspiration source to vary the aspiration force.

Clause 26: In some examples of the system of clause 25, the control circuitry is configured to vary the aspiration force by at least: intermittently varying the aspiration force; periodically varying the aspiration force; or pulsing the aspiration force.

Clause 27: In some examples, a method includes using a medical device to segment a thrombus, wherein the medical device includes an elongated body comprising an expandable member disposed at a distal portion of the elongated body, the elongated body further comprising an interior surface defining an inner lumen; a rotatable cutting tool located within an inner lumen of the elongated body, the rotatable cutting tool configured to segment a thrombus into smaller pieces while an aspiration force pulls the thrombus proximally into the inner lumen; and an intermediate structure oriented radially between the rotatable cutting tool and the interior surface of the elongated body, the intermediate structure configured to prevent the cutting tool from contacting the interior surface of the elongated body.

Clause 28: In some examples of the method of clause 27, using the medical device to segment the thrombus includes: navigating the elongated body to a target site within vasculature of a patient; distally inserting the cutting tool into the inner lumen of the elongated body and into the expandable member; deploying the cutting tool from a delivery configuration to a deployed configuration; and actuating a rotation of the cutting tool to segment the thrombus.

Clause 29: In some examples of the method of clause 28, using the medical device to segment the thrombus further includes: positioning a distal member on a distal side of the thrombus; and proximally withdrawing the distal member to push the thrombus into the expandable member.

Clause 30: In some examples, a medical device includes an elongated body defining an inner lumen and comprising an expandable member disposed at a distal portion of the elongated body; a rotatable cutting tool located within an inner lumen of the elongated body, the rotatable cutting tool configured to segment a thrombus into smaller pieces while an aspiration force pulls the thrombus proximally into the inner lumen; and a stopper configured to limit movement of the cutting tool distally past a distal end of the expandable member.

Clause 31: In some examples of the medical device of clause 30, the medical device further includes an intermediate structure oriented radially between the rotatable cutting tool and the interior surface of the elongated body, the intermediate structure configured to prevent the cutting tool from contacting the interior surface of the elongated body and to retain the cutting tool in an approximately radially central position within the inner lumen.

Clause 32: In some examples of the medical device of clause 31, the intermediate structure comprises a sheath that radially surrounds the cutting tool.

Clause 33: In some examples of the medical device of any of clauses 30-32, the cutting tool is configured to expand radially outward from a delivery configuration to a deployed configuration, and wherein the cutting tool is configured to rotate within a volume defined by the inner lumen.

Clause 34: In some examples of the medical device of clause 33, while the cutting tool is in the deployed configuration, the cutting tool is radially inwardly compressible.

Clause 35: In some examples of the medical device of any of clauses 30-34, the cutting tool comprises a brush including a plurality of bristles extending radially outward from an elongated support member.

Clause 36: In some examples of the medical device of clause 35, the bristles are substantially rigid.

Clause 37: In some examples of the medical device of clause 35 or clause 36, the brush tapers radially inwardly as it extends in a distal direction.

Clause 38: In some examples of the medical device of any of clauses 30-37, the stopper comprises a silicone plug disposed on the cutting tool.

Clause 39: In some examples of the medical device of any of clauses 30-38, the stopper comprises a fluid-expandable balloon.

Clause 40: In some examples of the medical device of any of clauses 30-39, the stopper is configured to engage with a lip extending radially inward from the interior surface of the elongated body.

Clause 41: In some examples of the medical device of any of clauses 30-40, the cutting tool is configured to self-expand.

Clause 42: In some examples of the medical device of any of clauses 30-41, the medical device further includes a distal member configured to apply a proximal force onto a distal side of the thrombus to push the thrombus into the expandable member.

Clause 43: In some examples of the medical device of clause 42, the distal member is configured to proximally compress the thrombus against a distal mouth of the expandable member in order to form a fluid-tight seal between the thrombus and the distal mouth to strengthen an effect of the aspiration force on the thrombus.

Clause 44: In some examples of the medical device of clause 42 or clause 43, the distal member is coupled to an elongated support member of the cutting tool.

Clause 45: In some examples of the medical device of any of clauses 42-44, the distal member is proximally and distally movable with respect to the cutting tool.

Clause 46: In some examples of the medical device of any of clauses 42-45, the distal member is configured to expand radially outward from a delivery configuration to a deployed configuration.

Clause 47: In some examples of the medical device of any of clauses 30-46, the cutting tool includes: an elongated support element; and a plurality of radial extensions hingeably coupled to the elongated support element.

Clause 48: In some examples of the medical device of clause 47, the radial extensions are configured to pivot radially outward.

Clause 49: In some examples of the medical device of clause 47 or clause 48, the plurality of radial extensions form an inverted-dome or evergreen-tree shape.

Clause 50: In some examples of the medical device of any of clauses 30-49, the elongated body comprises a catheter.

Clause 51: In some examples of the medical device of clause 50, the expandable member defines an expandable distal mouth of the catheter.

The examples described herein may be combined in any permutation or combination.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
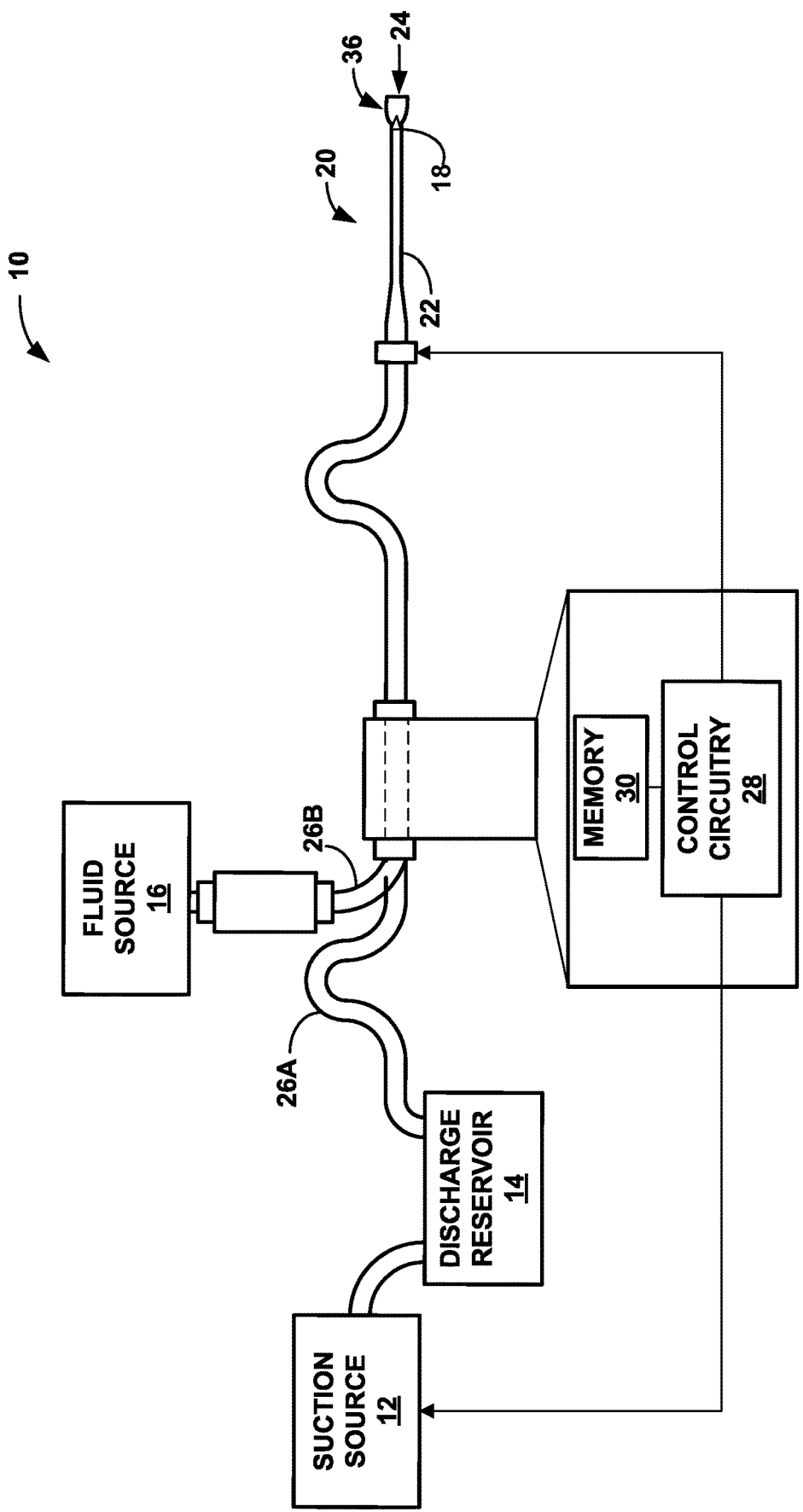
FIG. 1 is a schematic diagram illustrating an example medical aspiration system.

The disclosure describes a medical device, also referred to herein as a "catheter," including an expandable member configured to expand radially outward within a hollow anatomical structure (e.g., a blood vessel) of a patient, e.g., to engage with a thrombus to facilitate aspiration of the thrombus (e.g., a blood clot or other material such as a plaques or foreign bodies). The catheter also includes a mechanical cutting tool (also referred to herein as a "cutter") configured to segment at least a portion of a thrombus that is aspirated into an inner lumen of the catheter. As one non-limiting example, the mechanical cutter includes a plurality of bristle-like extensions projecting radially outward from a support member. The extensions are configured to rotate within an inner lumen of the catheter about a rotational axis to segment the thrombus.

In some examples, the mechanical cutting tool is configured to segment the thrombus as an aspiration force pulls the thrombus proximally into an inner lumen of the elongated body. For example, the mechanical cutter can be introduced into the inner lumen of the elongated body and positioned within, proximal to, or at least partially proximal to, the expandable member. In response to an aspiration force, a distal mouth of the expandable member envelops and retains a portion of the thrombus. In this configuration, the mechanical cutter can engage and segment the thrombus into smaller pieces to facilitate efficient aspiration through the elongated body.

In some examples, the catheter further comprises an intermediate structure configured to modulate a radial position of the mechanical cutter within the inner lumen of the catheter, a stopper configured to modulate a longitudinal or axial position of the cutter within the inner lumen of the catheter, and/or a distal element configured to mechanically compress the thrombus against a distal mouth of the catheter for segmentation within the inner lumen.

Example catheters in accordance with this disclosure include a relatively flexible elongated body configured to be navigated through vasculature of a patient, e.g., tortuous vasculature in a brain of the patient. The expandable member, such as an expandable stent-like structure or an expandable braid, is at a distal portion of the elongated body. In some examples, the expandable member is distinct from, but mechanically coupled to, the distal portion of the elongated body. In other examples, the expandable member is integrally formed with (e.g., laminated with and/or forming a distal extension of) the distal portion of the elongated body. The expandable member is configured to expand radially outward within a hollow anatomical structure (e.g., a blood vessel) of the patient. This may enable, for example, the expandable member to engage with a thrombus during an aspiration procedure, such as, but not limited to, a medical procedure using A Direct Aspiration first-Pass Technique (ADAPT) for acute stroke thrombectomy.

The expandable member may help improve aspiration of the thrombus into the catheter by providing a relatively large luminal diameter (and therefore exert a larger aspiration force against the thrombus or other material to be removed) and interior space for the thrombus to engage with the catheter compared to examples in which an otherwise similar catheter does not include an expandable member. For example, such a catheter that does not include an expandable member may have limited radial expansion due to a structural support member that extends to the distal end of the catheter, and may thus make it harder to aspirate a thrombus (e.g., due to a smaller cross-sectional dimension of the distal end of the catheter). The expandable member may overcome such radial expansion limitations, thereby increasing thrombus engagement, reducing the amount of time required for revascularization, and increasing revascularization success rates for various procedures, as compared to similar procedures performed using catheters that do not include an expandable member to engage a thrombus. Additionally, when implemented in concert with an applied aspiration force to proximally withdraw the thrombus into the inner lumen, the expandable member provides a clot-encapsulation region for the mechanical cutter to engage and segment the thrombus while simultaneously providing a barrier between, e.g., the mechanical cutter and the vasculature of the patient.

FIG. 1 is a schematic diagram illustrating an example medical aspiration system 10 including a suction source 12, a discharge reservoir 14, a fluid source 16, and an aspiration catheter 20. Aspiration system 10 may be used to treat a variety of conditions, including thrombosis. Thrombosis occurs when a thrombus (e.g., a blood clot or other material such as plaques or foreign bodies) forms and obstructs vasculature of a patient. For example, medical aspiration system 10 may be used to treat an ischemic insult, which may occur due to occlusion of a blood vessel (arterial or venous) that deprives brain tissue, heart tissue or other tissues of oxygen-carrying blood.

Aspiration system 10 is configured to remove fluid via catheter 20, e.g., draw fluid from catheter 20 into discharge reservoir 14, via a suction force applied by suction source 12 to catheter 20 (e.g., to an inner lumen of catheter 20). Catheter 20 includes an elongated body 22 defining a lumen (not shown in FIG. 1) terminating in a distal mouth 24. To treat a patient with thrombosis, a clinician may position distal mouth 24 of catheter 20 in a blood vessel of the patient near the thrombus or other occlusion, and apply a suction force (also referred to herein as suction, vacuum force, or negative pressure) to the catheter 20 (e.g., to one or more lumens of the catheter) to engage the thrombus with suction force at distal mouth 24 of catheter 20. For example, suction source 12 can be configured to create a negative pressure within the inner lumen of catheter 20 to draw a fluid, such as blood, an aspiration fluid, more solid material, or a mixture thereof, into the inner lumen via distal mouth 24 of catheter 20. The negative pressure within the inner lumen can create a pressure differential between the inner lumen and the environment external to at least a distal portion of catheter 20 that causes fluid and other material to be introduced into the inner lumen via distal mouth 24. For example, the fluid may flow from patient vasculature, into the inner lumen via distal mouth 24, and subsequently through aspiration tubing 26A (also referred to herein as "vacuum tube 26A") into discharge reservoir 14.

Once distal mouth 24 of aspiration catheter 20 has engaged the thrombus, the clinician may remove aspiration catheter 20 with the thrombus held within distal mouth 24 or attached to the distal tip of elongated body 22, or suction off pieces of the thrombus (or the thrombus as a whole) until the thrombus is removed from the blood vessel of the patient through a lumen of aspiration catheter 20 itself and/or through the lumen of an outer catheter in which aspiration catheter 20 is at least partially positioned. The outer catheter can be, for example, a guide catheter configured to provide additional structural support to the aspiration catheter. The aspiration of the thrombus may be part of an aspiration procedure, such as, but not limited to, a medical procedure using ADAPT for acute stroke thrombectomy, or any other procedure for aspiration of thrombus or other material from the neurovasculature or other blood vessels.

In addition, as discussed in further detail below, aspiration of thrombus can be performed concurrently with use of a mechanical cutting tool (or "cutter") 18 configured to segment a portion of a thrombus that is aspirated within the inner lumen at a distal portion of catheter 20.

In some examples, aspiration system 10 is also configured to deliver fluid from a fluid source 16, for example, a fluid reservoir different from discharge reservoir 14, through irrigation tubing 26B (also referred to herein as "irrigation tube 26B" or "flush tube 26B") and into the inner lumen of catheter 20 via a positive pressure applied by suction source 12.

As used herein, "suction force" is intended to include, within its scope, related concepts such as suction pressure, vacuum force, vacuum pressure, negative pressure, fluid flow rate, and the like. A suction force can be generated by a vacuum, e.g., by creating a partial vacuum within a sealed volume fluidically connected to a catheter, or by direct displacement of liquid in a catheter or tubing via (e.g.) a peristaltic pump, or otherwise. Accordingly, suction forces or suction as specified herein can be measured, estimated, computed, etc. without need for direct sensing or measurement of force. A "higher," "greater," or "larger" (or "lower," "lesser," or "smaller") suction force described herein may refer to the absolute value of the negative pressure generated by the suction source on catheter 20 or another component, such as a discharge reservoir 14.

In some examples, suction source 12 can comprise a pump (also referred to herein as "pump 12" or "vacuum source 12"). The suction source 12 can include one or more of a positive displacement pump (e.g., a peristaltic pump, a rotary pump, a reciprocating pump, or a linear pump), a direct-displacement pump (e.g., a peristaltic pump, or a lobe, vane, gear, or piston pump, or other suitable pumps of this type), a direct-acting pump (which acts directly on a liquid to be displaced or a tube containing the liquid), an indirect-acting pump (which acts indirectly on the liquid to be displaced), a centrifugal pump, and the like. An indirect-acting pump can comprise a vacuum pump, which displaces a compressible fluid (e.g., a gas such as air) from the evacuation volume (e.g., discharge reservoir 14, which can comprise a canister), generating suction force on the liquid. Accordingly, the evacuation volume (when present) can be considered part of the suction source. In some examples, suction source 12 includes a motor-driven pump, while in other examples, suction source 12 can include a syringe configured to be controlled by control circuitry 28, and mechanical elements such as linear actuators, stepper motors, etc. As further examples, the suction source 12 could comprise a water aspiration venturi or ejector jet.

Control of suction source 12 can comprise control, operation, and the like, of any one or combination of the component(s) making up the suction source. Accordingly, in examples in which suction source 12 includes a pump and an evacuation volume, control of the suction source can comprise control of only the pump, of only the evacuation volume, or of both of those components. As in examples in which suction source 12 includes only a pump, control of suction source 12 comprises control of the pump.

In some examples, suction source 12 is configured for bi-directional operation. For example, suction source 12 may be configured to create a negative pressure that draws fluid from the inner lumen of catheter 20 in a first flow direction and create a positive pressure that pumps fluid to catheter 20 and through inner the lumen in a second, opposite flow direction. As an example of this bi-directional operation, an operator of aspiration system 10 may operate suction source 12 to pump an aspiration/irrigating fluid, such as saline, from an aspiration fluid reservoir 16 via irrigation tube 26B to flush and/or prime catheter 20 (e.g., an infusion state) and subsequently draw fluid from a site of mouth 24 of catheter 20, such as saline and/or blood, via vacuum tube 26A, into discharge reservoir 14.

Aspiration system 10 includes control circuitry 28 configured to control a suction force applied by suction source 12 to catheter 20. For example, control circuitry 28 can be configured to directly control an operation of suction source 12 to vary the suction force applied by suction source 12 to the inner lumen of catheter 20, e.g. by controlling the motor speed, or stroke length, volume or frequency, or other operating parameters, of suction source 12. For instance, control circuitry 28 may vary the suction force by intermittently varying the aspiration force, by periodically varying the aspiration force, or by pulsing the aspiration force, as a few non-limiting examples.

As another example, control circuitry 28 can be configured to control a movement of mechanical cutter 18, which is configured to move according to a predetermined motion pattern to segment a portion of a thrombus that is aspirated into, and held within, a distal portion of the inner lumen of catheter 20. For instance, control circuitry 28 may be configured to actuate a rotational motion, a longitudinal motion, or a combination thereof, of mechanical cutter 18 within the inner lumen of catheter 20. Control circuitry 28 may actuate the motion of mechanical cutter 18 through any suitable motion mechanism, such as via a rotating cam, or via linear or rotary actuator(s) which can be electrically, electromagnetically, pneumatically or hydraulically driven to generate the desired movement of mechanical cutter 18. Such linear or rotary actuator(s) can be linear solenoid(s), rotary solenoid(s), or piezoelectric driven linear or rotary actuator(s). Regardless of the type of driving mechanism or actuator, control circuitry 28 may cause the motion mechanism to actuate the motion of mechanical cutter 18 according to a predetermined speed or frequency, or to vary within a range of speeds or frequencies. As a non-limiting example, control circuitry 28 may cause mechanical cutter to rotate, oscillate, or otherwise periodically move at a frequency from about 5000 Hertz (Hz) to about 50,000 Hz (or equivalently for rotational motion, from about 5000 revolutions per minute (rpm) to about 50,000 rpm).

Control circuitry 28, as well as other processors, processing circuitry, controllers, control circuitry, and the like, described herein, may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, control circuitry 28 may include multiple components, such as any combination of one or more microprocessors, one or more DSPs, one or more ASICs, or one or more FPGAs, as well as other discrete or integrated logic circuitry, and/or analog circuitry. In some examples, control circuitry 28 may further include, additionally or alternatively to electric-based processors, one or more controls that operate using fluid motion power (e.g., hydraulic power) in combination with or in addition to electricity. For example, control circuitry 28 can include a fluid circuit comprising a plurality of fluid passages and switches arranged and configured such that, when a fluid (e.g., a liquid or gas) flows through the passages and interacts with the switches, the fluid circuit performs the functionality of control circuitry 28 described herein.

Memory 30 may store program instructions, such as software, which may include one or more program modules, which are executable by control circuitry 28. When executed by control circuitry 28, such program instructions may cause control circuitry 28 to provide the functionality ascribed to control circuitry 28 herein. The program instructions may be embodied in software and/or firmware. Memory 30, as well as other memories described herein, may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

In the example shown in FIG. 1, control circuitry 28 is configured to control an amount of suction force applied by suction source 12 to the inner lumen of catheter 20. In some examples, suction source 12 is configured to apply a substantially continuous suction force (e.g., continuous or nearly continuous to the extent permitted by the hardware) to discharge reservoir 14, and the amount of this suction force that is transferred to the inner lumen of catheter 20 may be adjusted by control circuitry 28. As used herein, a "continuous" suction force may include a suction force having a relative strength that is generally constant over time, or that varies in strength such that distal mouth 24 experiences a constant pressure and/or a constant change in pressure to help pull thrombus portions into the inner lumen.

As detailed further below, a distal portion of elongated body 22 of catheter 20 includes an expandable member 36 configured to expand radially outward to widen distal mouth 24 for engaging with a thrombus. According to techniques of this disclosure, suction source 12, mechanical cutter 18, and expandable member 36 are configured to work in concert to provide improved thrombus engagement and removal. For example, while expandable member 36 is in an expanded configuration, suction source 12 may provide a continuous aspiration force within the inner lumen of expandable member 36, thereby engaging and retaining a thrombus against distal mouth 24. In some such examples, at least a proximal portion of the thrombus is proximally aspirated into the clot-encapsulation region provided by the inner lumen of expandable member 36, wherein mechanical cutter 18 may then segment the thrombus into smaller pieces that may then be aspirated proximally through elongated body 22.

Figure 2A:
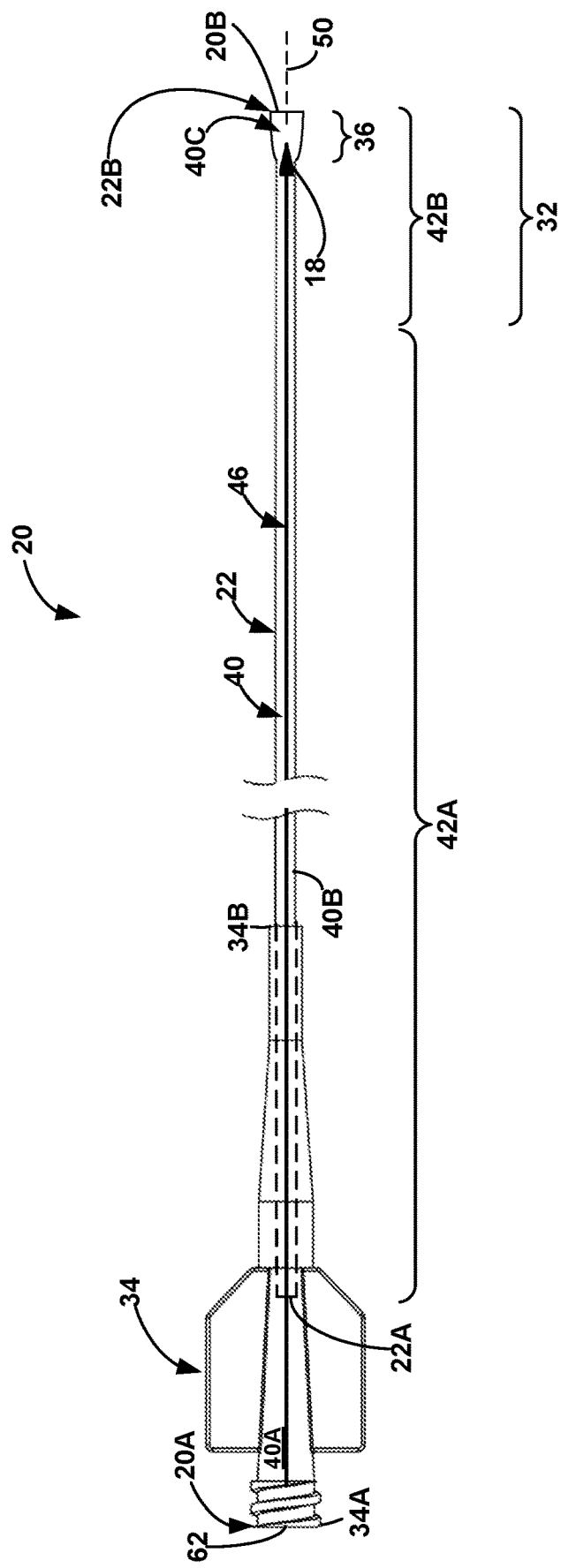
FIG. 2A is a conceptual side view of an example catheter of the medical aspiration system of FIG. 1, which includes an elongated body, an expandable member at a distal portion of the elongated body, and a mechanical cutting tool.
Figure 2B:
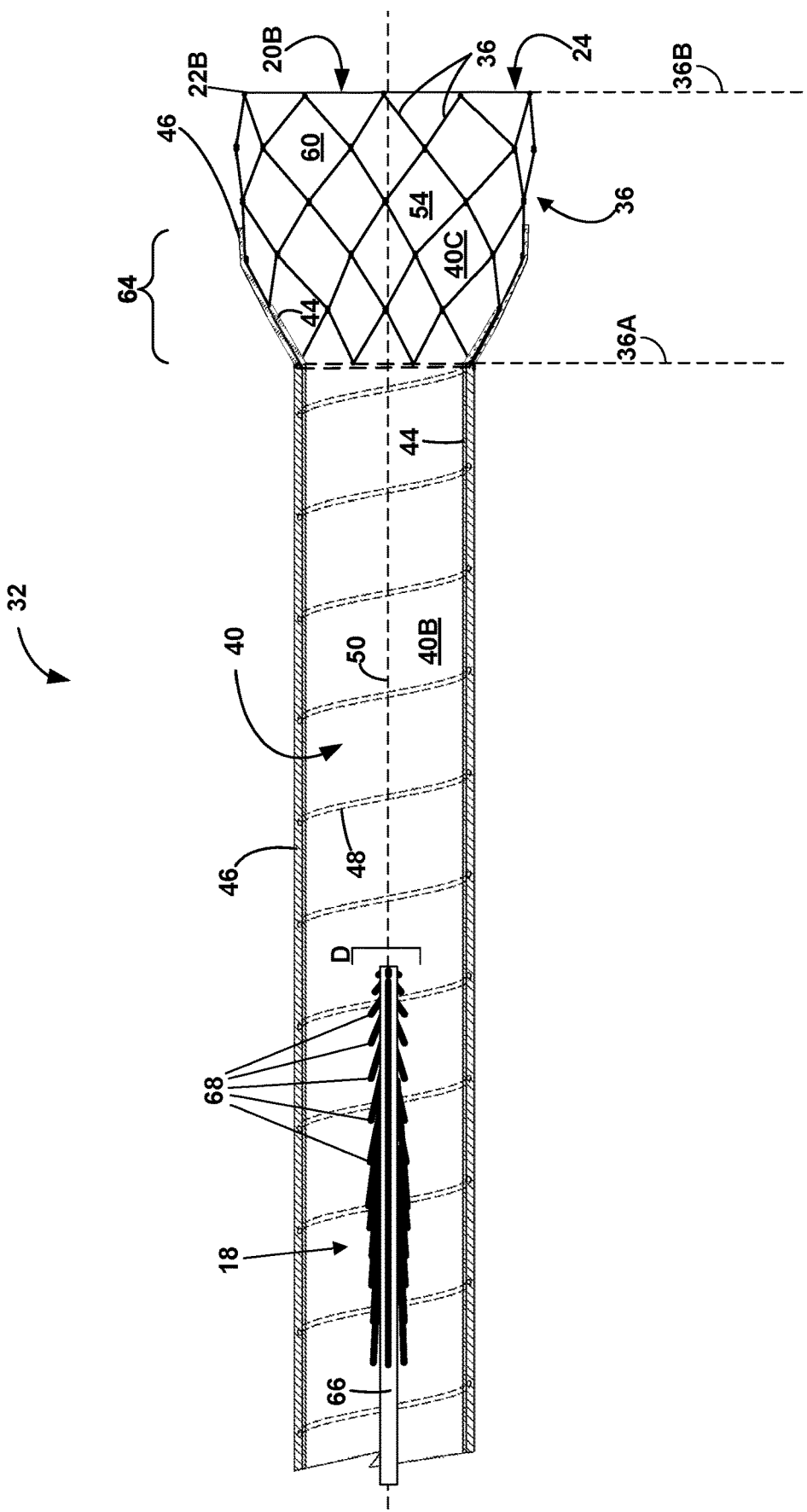
FIG. 2B is a conceptual cross-sectional view of an example of a distal portion of the catheter of FIG. 1, including the distal portion of the elongated body, the expandable member, and the mechanical cutting tool in a delivery configuration, where the cross-section is taken through a center of the catheter and along a longitudinal axis.

FIG. 2A is a conceptual side view of an example of catheter 20 of system 10 of FIG. 1, and FIG. 2B is a conceptual cross-sectional view of a distal portion 32 of the example catheter 20. As shown in FIGS. 2A and 2B, catheter 20 can include an elongated body 22, a hub 34, an expandable member 36, and a mechanical cutting tool 18. Catheter 20 defines an inner lumen 40, including a hub lumen 40A, a body lumen 40B, and an expandable member lumen 40C.

Elongated body 22 is configured to be advanced through vasculature of a patient via a pushing force applied to proximal body portion 42A (e.g., via hub 34) of elongated body 22 without buckling, kinking, or otherwise undesirably deforming (e.g., ovalization). As shown in FIG. 2B, elongated body 22 can include a plurality of concentric layers, such as an inner liner 44, an outer jacket 46, and a structural support member 48 (e.g., a coil, braid, and/or hypotube) positioned between inner liner 44 and outer jacket 46. For example, structural support member 48 can be positioned between inner liner 44 and outer jacket 46 along a full length of inner liner 44 and/or outer jacket 46 or only along part of the length. Elongated body 22 includes a proximal body portion 42A and a distal body portion 42B, which are each longitudinal sections of elongated body 22. Elongated body 22 extends from body proximal end 22A to body distal end 22B and defines at least one body lumen 40B (also referred to as a body inner lumen). In the example shown in FIG. 2A, proximal end 22A of elongated body 22 is received within hub 34 and is mechanically connected to hub 34 via an adhesive, welding, or another suitable technique or combination of techniques. Inner lumen 40 of catheter 20 may be defined by portions of hub 34, expandable member 36, and inner liner 44.

Catheter 20 may be used as an aspiration catheter to remove a thrombus or other material such as plaques or foreign bodies from vasculature of a patient. In such examples, a suction force (e.g., a vacuum) may be applied to proximal end 20A of catheter 20 (e.g., via hub 34) to draw a thrombus or other blockage into inner lumen 40. An aspiration catheter may be used in various medical procedures, such as a medical procedure to treat an ischemic insult, which may occur due to occlusion of a blood vessel (arterial or venous) that deprives brain tissue, heart tissue or other tissues of oxygen-carrying blood.

In some examples, catheter 20 is configured to access relatively distal locations in a patient including, for example, the middle cerebral artery (MCA), internal carotid artery (ICA), the Circle of Willis, and tissue sites more distal than the MCA, ICA, and the Circle of Willis. The MCA, as well as other vasculature in the brain or other relatively distal tissue sites (e.g., relative to the vascular access point), may be relatively difficult to reach with a catheter, due at least in part to the tortuous pathway (e.g., comprising relatively sharp twists or turns) through the vasculature to reach these tissue sites. Elongated body 22 may be structurally configured to be relatively flexible, pushable, and relatively kink- and buckle-resistant, so that it may resist buckling when a pushing force is applied to a relatively proximal section of catheter 20 (e.g., via hub 34) to advance elongated body 22 distally through vasculature, and so that it may resist kinking when traversing around a tight turn in the vasculature. In some examples, elongated body 22 is configured to substantially conform to the curvature of the vasculature. In addition, in some examples, elongated body 22 has a column strength and flexibility that allow at least distal body portion 42B of elongated body 22 to be navigated from a femoral artery, through the aorta of the patient, and into the intracranial vascular system of the patient, e.g., to reach a relatively distal treatment site.

Although primarily described as being used to reach relatively distal vasculature sites, catheter 20 may also be configured to be used with other target tissue sites. For example, catheter 20 may be used to access tissue sites throughout the coronary and peripheral vasculature, the gastrointestinal tract, the urethra, ureters, fallopian tubes, veins and other hollow anatomical structures of a patient.

Expandable member 36 is configured to radially expand within a vessel of a patient, e.g., to expand a distal mouth 24 of catheter 20 to enable catheter 20 to better engage a thrombus within the vessel. Expandable member 36 enables catheter 20 to exhibit the improved navigability characteristics of a catheter body with a relatively small diameter while still providing catheter 20 with the improved engagement and suction characteristics that may be attributed to having a large-diameter distal end 20B.

Expandable member 36 is positioned at distal body portion 42B of elongated body 22, such that a distal end 36B of expandable member 36 also defines distal end 20B of catheter 20 and distal mouth 24 open to inner lumen 40 of catheter 20. For example, expandable member lumen 40C (also referred to herein as an "expandable member inner lumen") may form a distal extension or distal portion of the body inner lumen 40B of elongated body 22. In these examples, expandable member lumen 40C is in fluid communication with inner lumen 40B of the elongated body 22.

In some examples, in its expanded states, expandable member 36 defines a tubular, cylindrical, or funnel shape configured to provide catheter 20 with a relatively large diameter (or other maximum cross-sectional diameter) distal end 20B (compared to, for example, proximal body portion 42A of elongated body 22) and interior space 40C for better encapsulation of, and engagement, with a thrombus (e.g., clot or embolus).

Expandable member 36 can include a frame configured to expand radially outward, thereby expanding lumen 40C radially outward. For example, the expandable frame can enable expandable member 36 to maintain its expanded shape (after it is expanded), even in the presence of a suction force applied to inner lumen 40 of catheter 20 during an aspiration process. Example expandable frames include an expandable-stent-like structure or an expandable tubular braid, weave, or mesh.

In any of these examples, expandable member 36 may include a flexible membrane 64 coupled to (e.g., radially inward and/or radially outward of) the expandable frame, or integrated into the expandable frame. In some examples, flexible membrane 64 may be formed of an elastomeric material, such as polyolefin thermoplastic elastomers, polyurethane elastomeric alloys or silicone, that permits the expansion of expandable member 36. In other examples, expandable member 36 does not include such flexible membrane 64.

Expandable member 36 can be configured to facilitate thrombus removal. In examples in which catheter 20 is used with an aspiration procedure, the size and shape of expandable member 36 may enable catheter 20 to better engage a thrombus by increasing the distal opening 24 into which the thrombus may be received, increasing the total aspiration force exerted on the thrombus via a larger luminal area, and/or by distributing the aspiration forces over a greater portion of the thrombus rather than a localized area, thereby allowing the thrombus to be aspirated into catheter 20 more effectively. Expandable member 36 enables catheter 20 to maintain a relatively small-diameter elongated body 22 (e.g., within proximal body portion 42A) to facilitate navigability of catheter 20, while also enabling catheter 20 to exhibit improved engagement and suction force characteristics that may be attributed to having a large-diameter distal end 20B. In some examples, the presence of expandable member 36 may lead to improved revascularization success rates, such as due to the improved thrombus engagement and/or suction (e.g., to better pull the entirety of the thrombus into catheter 20 during aspiration) as described herein.

Expandable member 36 may be of any suitable length and diameter, which may be selected based on the target vessel or particular procedure being performed. For example, expandable member 36 may be made be long enough to fully engulf a thrombus (e.g., an average amount of thrombus material), but short enough to avoid excessive friction between an outer surface of expandable member 36 and an inner surface of an introducer sheath or an outer catheter. In some examples, expandable member 36 may be about 2 centimeters to about 25 centimeters long, measured in a direction parallel to longitudinal axis 50. For example, expandable member 36 may be about 1.5 cm, about 2.0 cm, or about 25 cm in length, such as from about 0.5 cm to about 3.0 cm.

In some examples, distal end 20B of catheter 20 (or equivalently, distal end 36B of expandable member 36) may be about 110 percent to about 300 percent of the diameter of the proximal end 36A of expandable member 36. In some examples, the expanded outer diameter or the cross-sectional dimension of expandable member 36 at distal end 36B may be about 110 percent to about 130 percent of the diameter of elongated body 22 in a region proximal to expandable member 36. In other examples, expandable member 36 may expand to about 200 percent, 250 percent, 300 percent, or another larger percentage of the outer diameter or cross-sectional dimension of a more-proximal portion of elongated body 22.

Expandable member 36 is configured to expand from a collapsed configuration (also referred to herein as a "contracted," "compressed," or "delivery" configuration) to an expanded configuration (also referred to herein as a "deployed" configuration) using any suitable technique. In some examples, expandable member 36 may be balloon-expandable. For example, once elongated body 22 is positioned within the vessel of a patient adjacent a target treatment site, a balloon (not shown) may be introduced through lumen 40 of catheter 20 and inflated to radially expand expandable member 36 from a collapsed configuration to an expanded configuration.

In other examples, expandable member 36 may be configured to self-expand. For example, the expandable frame of expandable member 36 may be formed from a metal, and may include a shape-memory material such as Nitinol (and, optionally, additional material(s) or metal(s) such as radiopaque material(s) or metal(s)). In some such examples as described further below, an outer sheath can be positioned over expandable member 36 to retain expandable member 36 in a collapsed configuration, e.g., during navigation of elongated body 22 to a target treatment site within the vasculature of a patient. Once at the target treatment site, the outer sheath can be retracted or elongated body 22 may be extended distally outward from the sheath to allow expandable member 36 to self-expand. In other examples, catheter 20 may be navigated through vasculature with expandable member 36 already in an expanded state.

In other examples, an electrical energy may be used to expand expandable member 36. For example, expandable member 36 (or a portion or a layer thereof) may be formed from a material or metal that bends or deflects in response to a current passed therethrough (or to heat generated as a result of such current). One such type of material is shape memory alloy actuator material, e.g. Nitinol or Flexinol™ available from Dynalloy, Inc. of Irvine, California USA.

Hub 34 may be positioned at (e.g., proximal to or at least partially overlapping with) a proximal body portion 42A of elongated body 22. Proximal end 34A of hub 34 may define catheter proximal end 20A of catheter 20 and may include a proximal opening 62 aligned with inner lumen 40B of elongated body 22, such that inner lumen 40B of elongated body 22 may be accessed via proximal opening 62 and, in some examples, closed via proximal opening 62. For example, hub 34 may include a luer connector, a hemostasis valve, or another mechanism or combination of mechanisms for connecting hub 34 to another device such as vacuum source 12 (FIG. 1) for performing the aspiration techniques described herein. In some examples, proximal end 20A of catheter 20 can include another structure in addition to, or instead of, hub 34.

In some examples, inner liner 44 of elongated body 22 defines at least a portion 40B of inner lumen 40 of catheter 20, inner lumen 40B defining a passageway through elongated body 22. In some examples, inner lumen 40B may extend over the entire length of inner liner 44 (e.g., from proximal end 22A of elongated body 22 to distal end 22B). Inner lumen 40B may be sized to receive a medical device (e.g., another catheter, a guidewire, an embolic protection device, a stent, a mechanical cutting tool, or any combination thereof), a therapeutic agent, or the like. Elongated body 22, alone or with inner liner 44 and/or other structures, may define a single inner lumen 40, or multiple inner lumens (e.g., two inner lumens or three inner lumens) of catheter 20.

Inner lumen 40B formed at least by inner liner 44 may define an inner diameter of elongated body 22. The diameter of inner lumen 40B (as measured in a direction perpendicular to a longitudinal axis 50 of elongated body 22) may vary based on the one or more medical procedures with which catheter 20 may be used. In some examples, the diameter of inner lumen 40B of elongated body 22 may be substantially constant (e.g., constant or nearly constant) from proximal end 22A to distal end 22B or may taper (gradually or more step-wise) from a first inner diameter at proximal end 22A to a second, smaller inner diameter just proximal to expandable member 36. As described further below, the inner diameter of expandable member 36 may be larger than the inner diameter of elongated body 22 proximal to expandable member 36 while expandable member 36 is in an expanded configuration.

Inner liner 44 may be formed using any suitable material, such as, but not limited to, polytetrafluoroethylene (PTFE), expanded PTFE (ePTFE, e.g., unidirectional ePTFE or bi-directional ePTFE), a fluoropolymer, perfluoroalkyoxy alkane (PFA), fluorinated ethylene propylene (FEP), polyolefin elastomers, Low Density Polyethylene (LDPE) (e.g., about 42D), a PTFE having a durometer of about 60D, High Density Polyethylene (HDPE), or any combination thereof.

In some examples, one or more portions of the inner surface of inner liner 44 defining inner lumen 40B (and in some examples, the inner surface of expandable member 36 defining inner lumen 40C) may be lubricious to facilitate the introduction and passage of a medical device (e.g., another catheter, a guide member, an embolic protection device, a stent, a thrombectomy device, or any combination thereof), a therapeutic agent, a thrombus, or the like, through lumen 40B. A lubricious inner liner 44 may also enable relatively easy tracking of elongated body 22 over a guide member (e.g., a guidewire or a microcatheter). In some examples, the material from which portions of inner liner 44 is formed may itself be lubricious (e.g., PTFE). In addition to, or instead of, being formed from a lubricious material, in some examples, an inner surface of inner liner 44 is coated with a lubricious coating, such as a hydrophilic coating.

Elongated body 22 includes one or more structural support members 48 positioned over inner liner 44. Structural support member 48 is configured to increase the structural integrity of elongated body 22 while allowing elongated body 22 to remain relatively flexible. For example, structural support member 48 may be configured to help elongated body 22 substantially maintain its cross-sectional shape (e.g., circular or nearly circular) or at least help prevent elongated body 22 from buckling or kinking as it is navigated through tortuous anatomy. Additionally, or alternatively, structural support member 48, together with inner liner 44, and outer jacket 46, may help distribute both pushing and rotational forces along a length of elongated body 22, which may help prevent kinking of elongated body 22 upon rotation of body 22 or help prevent buckling of body 22 upon application of a pushing force to body 22. As a result, a clinician may apply pushing forces, rotational forces, or both, to the proximal portion of elongated body 22, and such forces may cause a distal portion of elongated body 22 to advance distally, rotate, or both, respectively.

Structural support member 48 may include one or more tubular braided structures, one or more coil members defining a plurality of turns, e.g., in the shape of a helix, one or more hypotubes, or a combination of one or more braided structures, one or more coil members, and/or one or more hypotubes. Thus, although the examples of the disclosure primarily describe structural support member 48 as a coil, in other examples, catheter 20 may include a braided structure instead of a coil, a braided structure in addition to a coil, or a combination that includes one or more of each structure. As one example, a proximal portion of structural support member 48 may include a braided structure and a distal portion of structural support member 48 may include a coil member.

Structural support member 48 can be made from any suitable material, such as, but not limited to, a metal (e.g., a nickel titanium alloy (Nitinol), stainless steel, tungsten, titanium, gold, platinum, palladium, tantalum, silver, or a nickel-chromium alloy, a cobalt-chromium alloy, or the like), a polymer, a fiber, or any combination thereof. In some examples, structural support member 48 may include one or more metal wires braided or coiled around inner liner 44. The metal wires may include round wires, flat-round wires, flat wires, or any combination thereof.

Structural support member 48 is positioned proximal to expandable member 36. In some examples, structural support member 48 and expandable member 36 are integrally formed. In other examples, expandable member 36 is mechanically coupled to structural support member 48 and/or layered between (at least in a proximal portion of the expandable member 36) inner liner 44 and outer jacket 46. For example, expandable member 36 and structural support member 48 can be formed independently of one another, and the proximal end of expandable member 36 may be coupled to the distal end of structural support member 48. In some examples, expandable member 36 and structural support member 48 may be joined via welding, brazing, soldering, adhesives, epoxy, mechanical connections (e.g., hooks), or other suitable technique.

In other examples, expandable member 36 may not be coupled to structural support member 48 or may not be in direct contact (e.g., abutting contact) with structural support member 48, although the two members may be in the same radial layer of elongated body 22 (and/or have the same inner diameter and/or outer diameter where structural support member 48 and expandable member 36 meet or come closest to each other in the longitudinal direction). For example, the distal end of structural support member 48 may be adjacent to the proximal end of expandable member 36 but separated by a small gap. In such examples, structural support member 48 and expandable member 36 may be in the same radial layer and inner liner 44, outer jacket 46, or both may secure both expandable member 36 and structural support member 48 in place along elongated body 22.

In some examples, structural support member 48 may be coupled, adhered, or mechanically connected to at least a portion of an outer surface of inner liner 44. For example, structural support member 48 may be positioned over inner liner 44 and secured in place (e.g., fixed) relative to inner liner 44 by outer jacket 46 using a melt-reflow/heat shrink process, via adhesives or other suitable technique. Additionally or alternatively, structural support member 48 may be secured to inner liner 44 with the assistance of a support layer (not shown) that helps adhere structural support member 48 to one or both of inner liner 44 and outer jacket 46. The support layer may include a thermoplastic material or a thermoset material, such as a thermoset polymer or a thermoset adhesive that bonds to inner liner 44, outer jacket 46, or both.

One or both of inner liner 44 or outer jacket 46 may extend over the entire length of expandable member 36 or may extend over only a portion of the length of expandable member 36. For example, flexible membrane 64 may include a distal portion of inner liner 44 extending over only part of the length of expandable member 36 leaving portions of expandable member 36 exposed to inner lumen 40C. The exposed portions of expandable member 36 may provide better engagement with a thrombus and/or prevent distal migration of thrombus from catheter 20 due to the texture of expandable member 36 or direct electrostatic engagement with expandable member 36.

In the example shown in FIG. 2B, outer jacket 46 is positioned over structural support member 48 and inner liner 44, the structural support member 48 being positioned between portions of inner liner 44 and outer jacket 46. In some examples, outer jacket 46 may be positioned around structural support member 48 such that outer jacket 46 covers at least a part or all of both inner liner 44 and structural support member 48. Outer jacket 46, together with inner liner 44 and structural support member 48, may be configured to define elongated body 22 having the desired structural characteristics (e.g., flexibility, kink resistance, torque responsiveness, structural integrity, pushability, and column strength, which may be a measure of a maximum compressive load that can be applied to elongated body 22 without taking a permanent set). For example, outer jacket 46 may have stiffness characteristics that contribute to the desired stiffness profile of elongated body 22.

In some examples, outer jacket 46 may be formed to have a stiffness that decreases from a proximal end 22A of elongated body 22 toward distal end 22B. The lowered stiffness of outer jacket 46 within the distal body portion 42B of elongated body 42 may improve the flexibility and navigability of catheter 20 through tortious vasculature of the patient, while the relatively higher stiffness of outer jacket 46 within the proximal body portion 42A of catheter 20 may provide better pushability or kink resistance. In some examples, outer jacket 46 may be formed from two or more different materials with different mechanical properties that enable outer jacket 46 to exhibit the desired stiffness characteristics. In some examples outer jacket 46 may define a stiffness that is greater than the stiffness of flexible membrane 54 of expandable member 36.

In some examples, outer jacket 46 may be formed using any suitable material including, but are not limited to, polymers, such as a polyether block amide (e.g., PEBAX®, commercially available from Arkema Group of Colombes, France), an aliphatic polyamide (e.g., Grilamid®, commercially available from EMS-Chemie of Sumter, South Carolina), another thermoplastic elastomer (e.g., a thermoplastic, elastomeric polymer configured to accommodate radial expansion of expandable member 36), polyurethanes, polyamides, or other thermoplastic material, or combinations thereof.

Outer jacket 46 may be heat-shrunk around structural support member 48 and, in some examples, at least a portion (e.g., a proximal portion) of expandable member 36 to secure the two members 36, 48 in the same radial layer. In some examples, during the heat shrinking of outer jacket 46 around structural support member 48, the material of outer jacket 46 may flow into at least some of the inner spacings or gaps (e.g., gaps between the adjacent turns of the coils, or between the struts or braids) within structural support member 48 or expandable member 36 such that portions of outer jacket 46, structural support member 48, and/or expandable member 36 form a laminated structure.

In some examples, at least a portion of an outer surface of outer jacket 46 and/or expandable member 36 includes one or more coatings, such as, but not limited to, an antithrombogenic coating, which may help reduce the formation of thrombi in vitro, an anti-microbial coating, and/or a lubricating coating.

Although a coating or another material may be applied over the outer surface of outer jacket 46, outer jacket 46 may still substantially define a shape and size of the outer surface of elongated body 22. In some examples, the outer diameter of elongated body 22 may be substantially constant (e.g., constant or nearly constant) along the length of elongated body 22. In other examples, the outer diameter of elongated body 22 may taper from the first outer diameter within proximal body portion 42A of elongated body 22 to a second outer diameter at a point proximate to the proximal end 36A of expandable member 36.

In some examples, both inner liner 44 and outer jacket 46 terminate proximal to a distal end of expandable member 36. In other examples, inner liner 44 and outer jacket 46 can have other arrangements relative to expandable member 36.

Catheter 20 includes a mechanical cutting tool, or "cutter," 18, configured to be disposed (e.g., introduced and positioned) within inner lumen 40 of catheter 20 and remain within inner lumen 40 during an aspiration procedure. Mechanical cutter 18 is configured to move to segment portions of a thrombus that contact mechanical cutter 18, e.g., thrombus portions that become aspirated into inner lumen 40 through distal mouth 24. As one non-limiting example, mechanical cutter 18 may be configured to rotate about central longitudinal axis 50 of catheter 20 or another rotational axis in order to cut the thrombus portions into smaller portions. In other examples, mechanical cutter 18 may additionally or alternatively be configured to oscillate proximally and distally in order to segment the thrombus into smaller portions. In other examples, mechanical cutter 18 may be configured to move according to other motion patterns, or any combination thereof.

FIGS. 2A and 2B depict a first example configuration of mechanical cutter 18. In the example depicted in FIGS. 2A and 2B, mechanical cutter 18 includes a brush-type configuration including an elongated support structure 66 and a plurality of brush-like bristles 68 extending radially outward from support structure 66. However, this example configuration is not intended to be limiting. Mechanical cutter 18 can have any suitable configuration for engaging and segmenting a thrombus within a patient's vasculature. For instance, in other examples, mechanical cutter 18 may include a corkscrew-type or auger-type radial extension that wraps helically around an outer circumference of support structure 66.

In some examples, any or all of bristles 68 (or other similar elongated extensions of mechanical cutter 18) are configured to extend outward from support structure 66 at an angle other than perpendicular to central longitudinal axis 50 when support structure 66 is substantially longitudinally aligned (e.g., longitudinally aligned or within 5-10 degrees or less) with central longitudinal axis 50.

Each of bristles 68 may define an individual bristle length (e.g., as measured from an end connected to support structure 66 to a free end, e.g., in a radial direction in some examples described herein) such that the outer-most ends of bristles 68 (e.g., the free ends of bristles 68 that are not rigidly coupled to support structure 66) collectively define a geometric shape of mechanical cutter 18. In the example depicted in FIGS. 2A, 2B, 3A, and 4-7, the outer-most ends of bristles 68 define a generally conical shape or evergreen-tree shape, having a generally circular outer circumference (along a planar cross-section taken orthogonal to central longitudinal axis 50) that tapers in a distal direction. In other examples, such as the example depicted in FIG. 3B, the outer-most ends of bristles 68 define a generally conical shape or evergreen-tree shape that tapers in a proximal direction (e.g., that widens in circumference along a distal direction). In other examples, bristles 68 can collectively define virtually any two-dimensional or three-dimensional geometric shape. As another example, bristles 68 may taper in a distal direction according to a non-linear pattern so as to collectively define a hemispherical shape or dome-shape (e.g., an open umbrella shape).

In some examples, bristles 68 are relatively rigid, forming a blender-type mechanism when mechanical cutter 18 is actuated. In other examples, bristles 68 may be flexible (e.g., non-self-supporting wires, fibers, or the like), forming a weed-wacker-type mechanism to segment the thrombus when mechanical cutter 18 is actuated.

In some examples herein, similar to expandable member 36, mechanical cutter 18 may be configured to transition between a collapsed, contracted, or delivery configuration (depicted in FIG. 2B), and an expanded or deployed configuration (depicted in FIG. 2A and FIGS. 3A-7). For example, as depicted in FIG. 2B, in examples in which mechanical cutter 18 includes a plurality of elongated bristles 68, bristles 68 may be configured to hingedly revolve or collapse radially inward toward support structure 66 in order to reduce a maximum outer dimension, e.g., diameter "D," of mechanical cutter 18 for delivery of mechanical cutter 18 distally through inner lumen 40 of catheter 20. Once mechanical cutter 18 is positioned at a desired location within inner lumen 40, mechanical cutter 18 may be expanded to the deployed configuration, depicted in FIG. 2A and FIGS. 3A-7, through any suitable means, such as means similar to those described above with respect to expandable member 36. As one non-limiting example, mechanical cutter 18 may include a pull wire (not shown) configured to re-orient bristles 68 relative to support structure 66. While in the deployed configuration, mechanical cutter 18 is then radially inwardly compressible back to the delivery configuration, either via the same mechanism (e.g., a pull wire) or another mechanism.

As another example, bristles 68 and/or support structure 66 may be (e.g., integrally) formed from a shape-memory material, such as Nitinol, into a shape in which bristles 68 are inclined to extend radially outward into the expanded configuration shown, e.g., in FIGS. 1, 2A, 3A, and 3B. In some such examples, bristles 68 may fold down into the compressed or delivery configuration when introduced into lumen 40A, e.g., in response to contact with the interior surface of elongated body 22 or another structure, as detailed further below. Bristles 68 may then self-expand radially outward into the expanded configuration of mechanical cutter 18 when sufficient space is available, for instance, when advanced into a wider portion of inner lumen 40B, 40C, etc.

Mechanical cutter 18 is configured to be used in conjunction with an aspiration force, as described above. For instance, as detailed below with respect to FIG. 7, a medical system may include aspiration source 12 of FIG. 1 (e.g., a vacuum) configured to at least partially proximally withdraw a thrombus through a distal mouth 24 of catheter 20 and into lumen 40C of expandable member 36 and/or lumen 40B of elongated body 22. While held within lumen(s) 40B, 40C by the aspiration force, mechanical cutter 18 is configured to engage with and segment the thrombus, e.g., to remove a thrombus portion from the remainder of the thrombus body located external and distal to lumen(s) 40B, 40C.

Figure 3A:
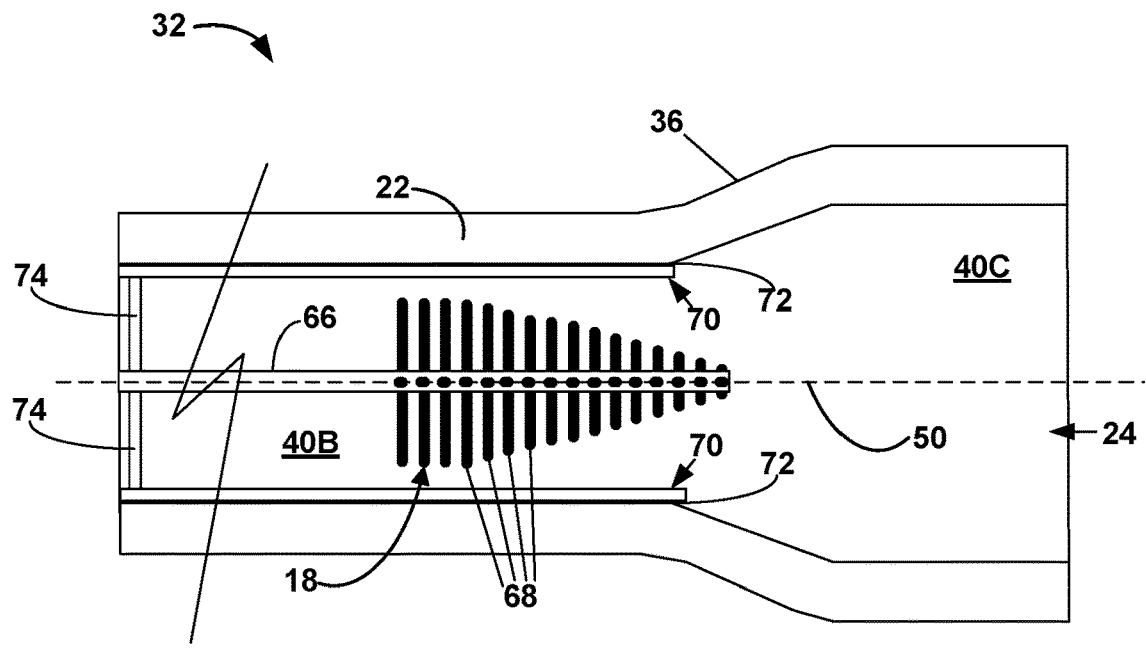
FIG. 3A is a conceptual cross-sectional view of another example of the distal portion of the catheter of FIG. 1 showing the cutting tool in a deployed configuration and an example intermediate structure, where the cross-section is taken through a center of the catheter and along a longitudinal axis.

In some examples, catheter 20 includes additional structural elements configured to modulate or otherwise control a relative position and/or orientation of mechanical cutter 18 within inner lumen 40 of catheter 20. Structural elements may include, for example, an intermediate structure configured to modulate a radial position of mechanical cutter 18 within inner lumen 40, and a stopper element configured to modulate an axial or longitudinal position of mechanical cutter 18 within inner lumen 40. For instance, FIG. 3A is a conceptual cross-sectional view of another example of the distal portion 32 of catheter 20 of FIG. 1 showing mechanical cutting tool 18 in a deployed configuration, where the cross-section is taken through a center of the catheter and along longitudinal axis 50. In the example depicted in FIG. 3A, catheter 20 includes an intermediate structure 70 positioned radially outward (relative to central longitudinal axis 50) from at least a portion of cutting tool 18 (e.g., just a proximal portion or an entire length of cutting tool 18), and positioned radially inward from at least a portion of interior surface 72 of elongated body 22. Interior surface 72 can be, for example, an interior surface of inner liner 44 defining body lumen 40B.

In the example depicted in FIG. 3A, intermediate structure 70 is depicted as an elongated hollow sheath radially surrounding mechanical cutter 18. In other examples, intermediate structure 70 can have any suitable physical configuration configured to perform the functions described below. In examples in which intermediate structure 70 comprises an elongated sheath, an exterior surface of the sheath may be sized or otherwise configured to substantially conform to interior surface 72 of elongated body 22, thereby reducing or eliminating a gap between the surfaces that could otherwise receive and retain undesired portions of segmented thrombus material. This may enable, for example, all or most of the thrombus to move (under an aspiration force) proximally through an inner lumen of intermediate structure 70, rather than through a radial space between an outer surface of intermediate structure 70 and interior surface 72 of elongated body 22.

As one example function of intermediate structure 70, intermediate structure 70 may be configured to radially surround all or part of mechanical cutter 18, such as one or more (or all) of the segmenting bristles 68 of mechanical cutter 18, in order to prevent bristles 68 or other similar structure of mechanical cutter 18 from contacting the interior surface 72 of elongated body 22 while mechanical cutter 18 is actuated, e.g., is in motion. In other words, intermediate structure 70 is configured to reinforce and protect elongated body 22 from abrasive forces conveyed by mechanical cutter 18. In some such examples, intermediate structure 70 may be made from a material that is substantially scratch-resistant or otherwise durable, e.g., more durable than an inner surface of elongated body 22.

As another example function, intermediate structure 70 may be configured to radially fix or center mechanical cutter 18 at a desired radial position (relative to central longitudinal axis 50) within inner lumen 40B of elongated body 22. For example, as shown in FIG. 3A, intermediate structure 70 may be rigidly coupled to mechanical cutter 18 via a centering mechanism, such as centering extensions 74, in order to suspend and approximately center cutting tool 18 within inner lumen 40 of elongated body 22. In example catheters without a similar centering structure 74, mechanical cutter 18 would be capable of moving radially relative to interior surface 72 of elongated body 22 (or the inner surface of intermediate structure 70, if present), thereby applying mutual friction between mechanical cutter 18 and the respective inner surface, and retarding a movement, such as a rotational motion, of mechanical cutter 18, and reducing the thrombus-segmentation efficacy of mechanical cutter 18.

Centering structure 74 may be positioned at any suitable axial position along an axial length of support structure 66. As shown in FIG. 3A, centering structure 74 may be positioned at a relatively proximal position within inner lumen 40. In other examples, centering structure may be located at a more distal position within inner lumen 40, e.g., closer to bristles 68. In other examples, catheter 20 may include a plurality of centering structures 74 spaced along the axial length of support structure 66. Centering structure 74 can have any suitable configuration, e.g., one or more relatively rigid flanges that help support structure 66 maintain a desired position within inner lumen 40. Centering structure 74 is configured to enable fluid and a thrombus or segmented thrombus portions move proximally past centering structure 74, e.g., to discharge reservoir 14 (FIG. 1).

Intermediate structure 70 can have any suitable length measured along longitudinal axis 50. In some examples, intermediate structure 70 extends a full length of support structure 66 and to a distal-most end of cutting tool 18. In other examples, intermediate structure 70 extends only along a distal portion of cutting tool 18, e.g., around some or all of bristles 68 in the example shown in FIG. 3A. Cutting tool 18 can be moved independently of intermediate structure 70 in some examples. For example, cutting tool 18 can be advanced through intermediate structure 70. In other examples, intermediate structure 70 and cutting tool 18 are coupled together and configured to move longitudinally together through inner lumen 40 of catheter 20.

Figure 4:
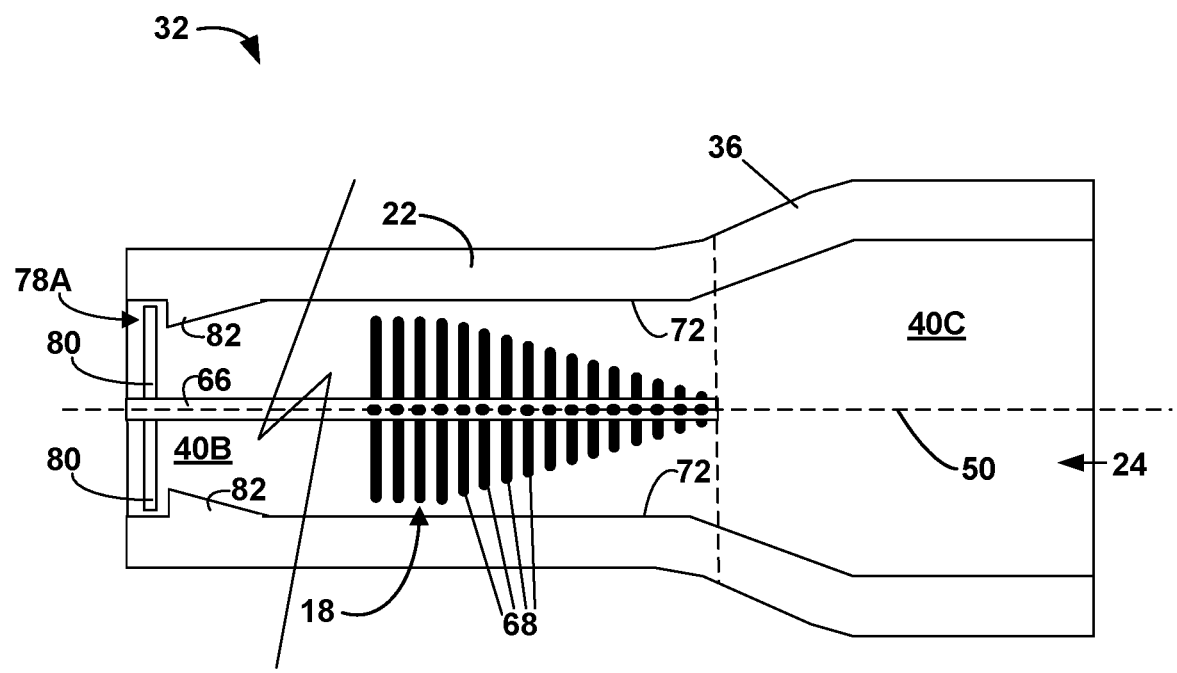
FIGS. 4-6 are conceptual cross-sectional views of three examples of the distal portion of the catheter of FIG. 1 showing the cutting tool in a deployed configuration and example stoppers, where the cross-sections are each taken through a center of the catheter and along a longitudinal axis.
Figure 5:
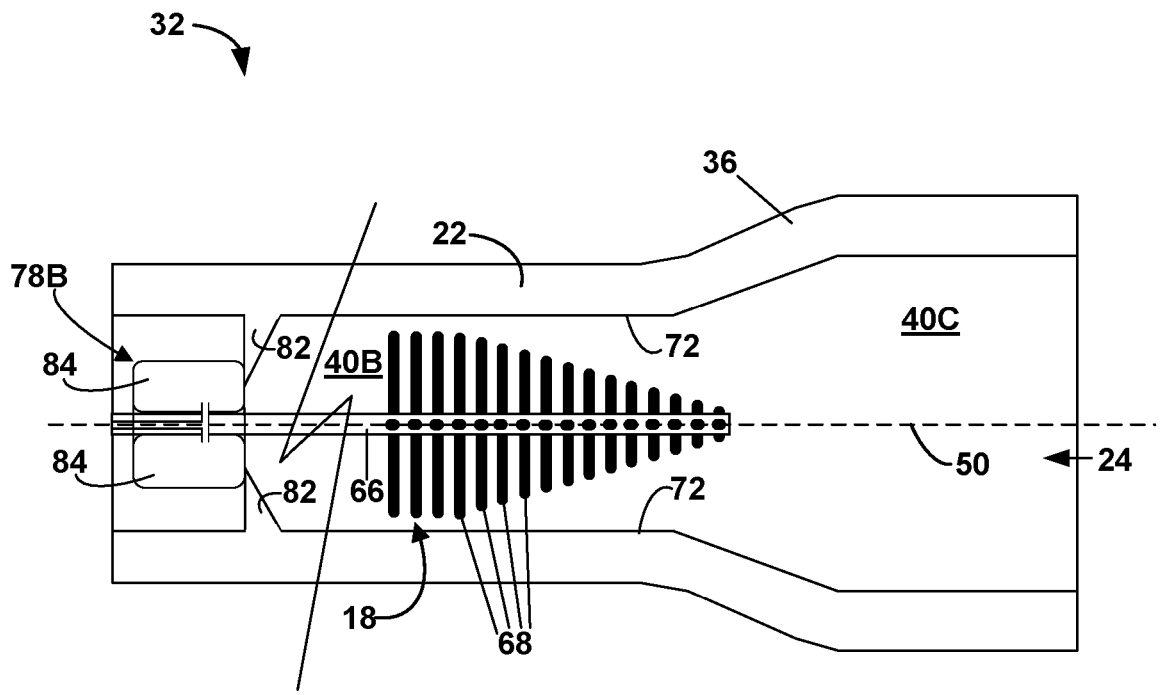
Figure 6:
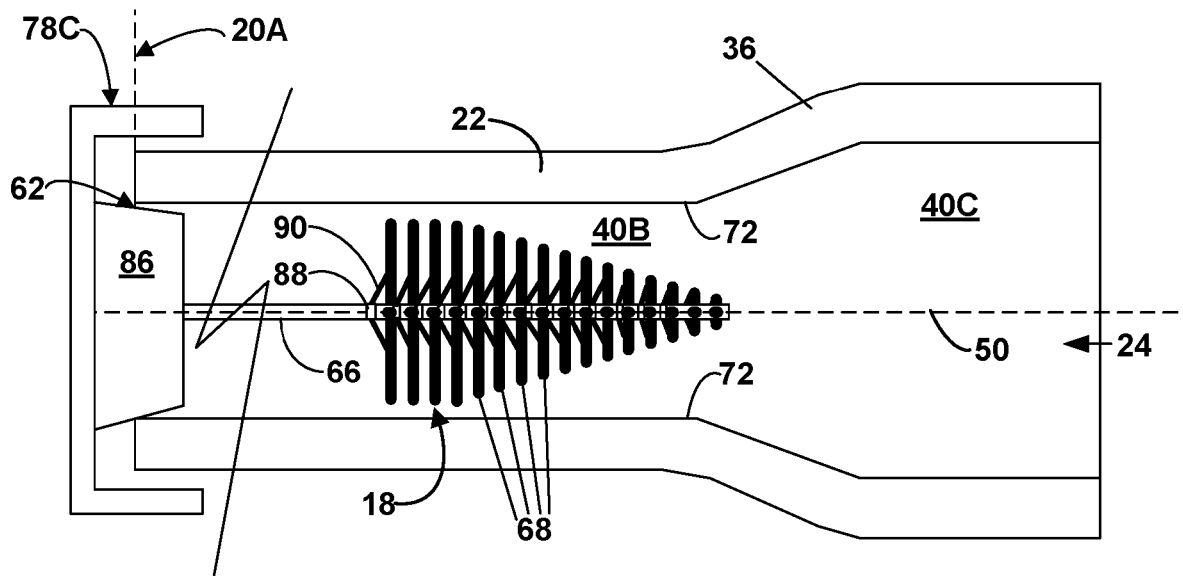

Additionally or alternatively to an intermediate structure configured to modulate a radial position of mechanical cutter 18, catheter 20 may include a stopper mechanism configured to modulate an axial or longitudinal position of mechanical cutter 18 within inner lumen 40. For instance, FIGS. 4-6 are conceptual cross-sectional views of three examples of the distal portion 32 of the catheter 20 of FIG. 1, showing the cutting tool 18 in a deployed configuration, where the cross-sections are each taken through a center of the catheter 20 and along a longitudinal axis 50. Each of FIGS. 4-6 further illustrates an example of a stopper mechanism 78A-78C (also referred to in general herein as "stopper 78") configured to modulate an axial position of mechanical cutter 18 relative to the inner lumen 40 of elongated body 22. While mechanical cutter 18 may generally be configured to move proximally and distally within inner lumen 40 of elongated body 22, each stopper 78 is configured to prevent mechanical cutter 18 from extending distally past a predetermined point. For example, stopper 78 may be configured to prevent cutting tool 18 from extending distally into inner lumen 40C of expandable member 36. In other examples, stopper 78 may be configured to enable mechanical cutter 18 to extend distally into inner lumen 40C of expandable member 36, but further configured to prevent mechanical cutter 18 from extending distally outward from distal mouth 24 of expandable member 36. Although described and depicted herein as distinct structures, it is to be understood that any of stoppers 78 may be coupled to, may be integrated with, or may be the same structure as intermediate structure 70 and/or centering structure 74 (FIG. 3A).

Figure 3B:
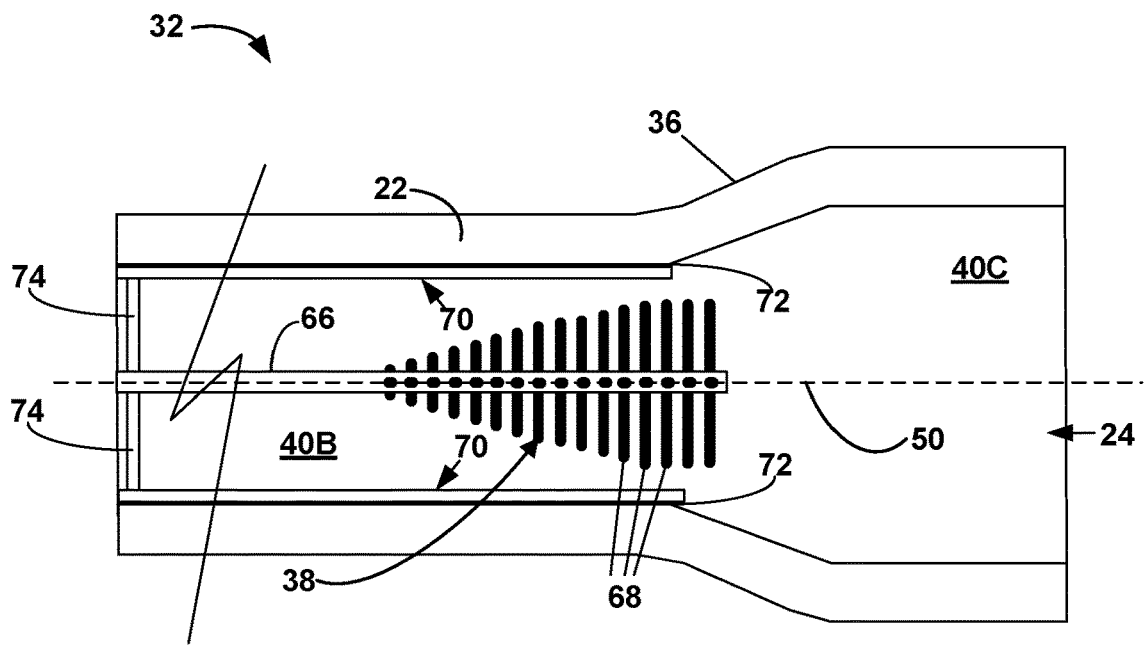
FIG. 3B is a conceptual cross-sectional view of another example of the distal portion of the catheter of FIG. 1 showing the cutting tool in a deployed configuration and an example intermediate structure, where the cross-section is taken through a center of the catheter and along a longitudinal axis.

FIG. 3B is a conceptual cross-sectional view of another example of the distal portion 32 of catheter 20 of FIG. 1 showing a mechanical cutting tool 38 in a deployed configuration, where the cross-section is taken through a center of the catheter and along longitudinal axis 50. Cutting tool 38 may be an example of cutting tool 18 of FIGS. 1-3A, except for the differences noted herein. For instance, as depicted in FIG. 3B, bristles 68 of cutting tool 38 collectively define (e.g., via their radially outer-most ends) a generally conical shape or evergreen-tree shape that tapers in a proximal direction, instead of in the distal direction, as depicted in FIGS. 1-3A. Different configurations and orientations of cutting tools 18, 38, e.g., of bristles 68, may provide additional benefits with respect to aspiration of a thrombus or other occlusive material. For instance, certain configurations of bristles 68 may help prevent a clogging of inner lumen 40B as thrombus material is aspirated into the inner lumen. For instance, in some examples, cutting tool 18 may extend distally into expandable member 36, thereby providing for more volume around cutting tool 38. In some such examples, a tapering of bristles 68 along a distal direction (such that cutting tool 38 increases in diameter or other maximum cross-sectional dimension in a direction away from the distal end of cutting tool 18) may help reduce or minimize the extent to which cutting tool 18 blocks aspiration force applied to distal mouth 24 of catheter 20.

FIG. 4 depicts a first example stopper 78A, as described above with respect to FIG. 3A. Stopper 78A includes one or more radial extensions 80 extending radially outward from support structure 66. In the example depicted in FIG. 4, radial extensions 80 are sized to fit within inner lumen 40B of elongated body 22 and enable fluid and thrombus flow proximally past radial extensions 80. In such examples, interior surface 72 of elongated body 22 may include a corresponding lip 82 extending radially inward into inner lumen 40B of elongated body 22. Lip 82 may be sized (in a radial direction) so as to enable bristles 68 of mechanical cutter 18 to extend axially past lip 82, but also sized (in a radial direction) to engage with radial extensions 80. In other examples, radial extensions 80 may be sized so as to not fit within inner lumen 40B of elongated body 22, but instead, to remain external to elongated body 22 and to engage with a proximal-most end 20A (FIG. 1) of catheter 20 to prevent mechanical cutter 18 from extending distally past a desired point within inner lumen 40.

FIG. 5 depicts another example stopper 78B. Stopper 78B includes one or more fluid-expandable balloons extending radially outward from support structure 66. In the example depicted in FIG. 5, balloons 84 are sized to fit within inner lumen 40B of elongated body 22, and further, are variably-expandable according to an amount of fluid injected through an inner lumen of support structure 66. In such examples, interior surface 72 of elongated body 22 may include a corresponding lip 82 extending radially inward into inner lumen 40B of elongated body 22. Lip 82 may be sized (in a radial direction) so as to enable bristles 68 of mechanical cutter 18 to extend axially past lip 82 (at least while in a delivery configuration of mechanical cutter 18), but also sized (in a radial direction) to engage with expandable balloons 84 to limit distal movement of mechanical cutter 18.

In the example depicted in FIG. 5, lip 82 may have a tapered configuration, wherein the lip extends more radially inward into inner lumen 40B along a distal direction. In such examples, the clinician may select and control an axial position at which expandable balloons 84 engage with lip 82, by injecting an amount of fluid into balloons 84 to control a desired size of balloons 84, corresponding to an axial position at which balloons 84 engage with lip 82, preventing mechanical cutter 18 from extending distally past this axial position.

In other examples, radial extensions 80 may be sized so as to not fit within inner lumen 40B of elongated body 22, but instead, to remain external to elongated body 22 and to engage with a proximal-most end 20A of catheter 20 to prevent mechanical cutter 18 from extending distally past a desired point within inner lumen 40. In some examples, a portion or all of stopper 78 may be configured to remain external to lumen 40. For instance, FIG. 6 depicts a third example stopper 78C. Stopper 78C includes a plug 86 coupled to support structure 66 and configured to engage with a proximal portion of catheter 20, such as with proximal end 20A. Proximal end 20A in FIG. 2A can be, for example, another opening into inner lumen 40, e.g., defined by hub 34, and separate from a proximal opening that is fluidically coupled to suction source 12 (FIG. 1).

In some examples, stopper 78C is configured to engage with proximal end 20A in order to close or cover proximal opening 62 to inner lumen 40A, in some instances, forming a fluid-tight seal over proximal opening 62. For instance, stopper 78C may be formed from a flexible material, such as silicone, to conform to the geometry of proximal opening 62, thereby forming the fluid-tight seal. In other examples, stopper 78C (or any of the stoppers 78 described herein) may be formed from a porous material, such as a porous mesh, enabling segmented thrombus portions or other fluids (e.g., saline, etc.) to pass therethrough.

Further illustrated in FIG. 6 is another example mechanism for converting mechanical cutter 18 between the delivery configuration (e.g., as shown in FIG. 2) and the deployed configuration. As shown in FIG. 6, each set of longitudinally aligned bristles 68 includes a corresponding runner 88 and set of mechanical stretchers 90, collectively forming an umbrella-type mechanism for expanding bristles 68 radially outward, away from support structure 66. Each runner 88 may be coupled to a pull wire (not shown) or other similar mechanism enabling a user (e.g., a clinician) to operate the umbrella-type mechanism from a position proximal to catheter 20, such as external to a patient while catheter 20 is inserted within a vasculature of a patient.

Figure 7:
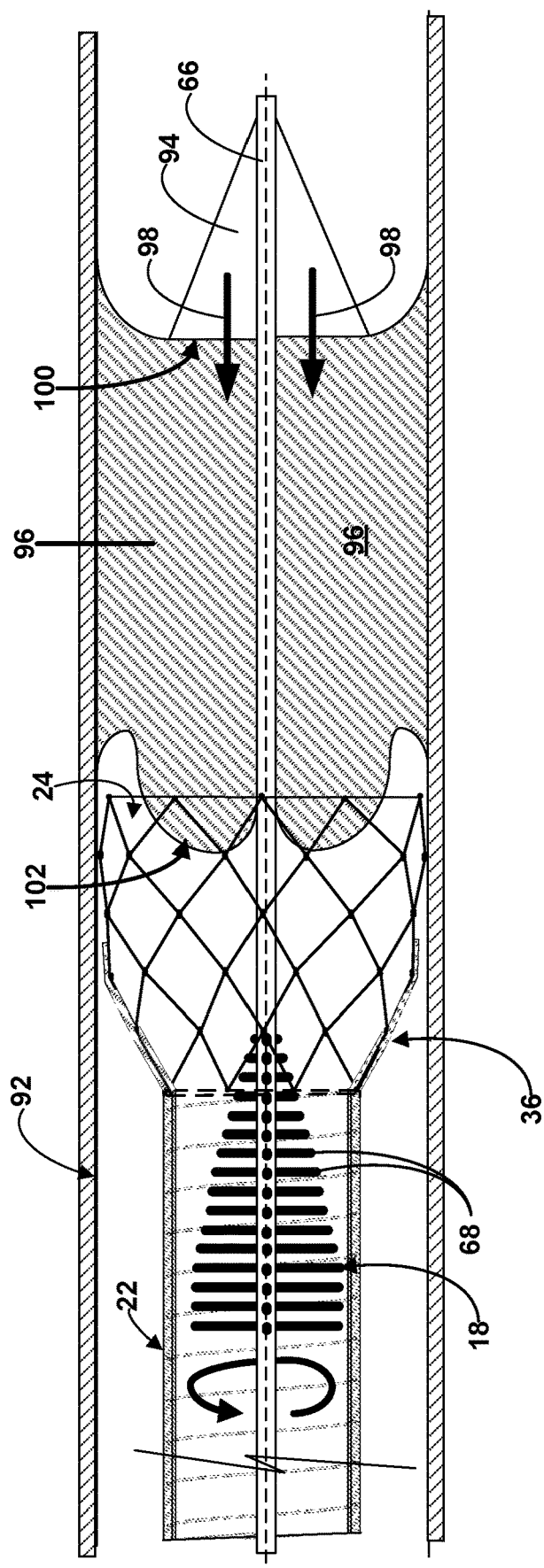
FIG. 7 is a conceptual cross-sectional view of another example of the distal portion of the catheter of FIG. 1 while introduced within vasculature of a patient, showing the cutting tool in a deployed configuration and an example distal element, where the cross-section is taken through a center of the catheter and along a longitudinal axis.

FIG. 7 is a conceptual cross-sectional view of another example of the distal portion 32 of the catheter 20 of FIG. 1 while introduced within vasculature 92 of a patient with mechanical cutting tool 18 in a deployed configuration. FIG. 7 further illustrates an example distal element 94 of catheter 20, in accordance with techniques of this disclosure. For instance, any of the above-described examples of catheter 20 may additionally or alternatively include a distal element 94 configured to apply a proximal force (indicated in FIG. 7 by proximal-facing arrows 98) onto a distal side of thrombus 96 in order to bias thrombus 96 proximally toward and into distal mouth 24 of catheter 20.

As shown in FIG. 7, distal element 94 may be a component of mechanical cutter 18, such as through a mechanical coupling to support structure 66. In other examples, distal element 94 may be slidably coupled to support structure 66, such that distal element is proximally and distally movable with respect to bristles 68 of mechanical cutter 18 (e.g., via a separate pull wire or other similar mechanism). In other examples, mechanical cutter may be coupled to other components of catheter 20, such as elongated body 22, or in other examples, may be a standalone (e.g., removably separable) element.

As used herein, distal element 94 may include any suitable physical structure that includes a proximal-facing surface 100 configured to contact and apply a proximal force 98 onto thrombus 96. In some examples, but not all examples, distal element 94 may be configured to convert between a delivery configuration and a deployed configuration (e.g., the configuration shown in FIG. 7), according to any suitable mechanism, such as a mechanism similar to any those described above with respect to expandable member 36 and mechanical cutter 18.

During use, a clinician may navigate distal end 20B of catheter 20 toward thrombus 96. Once distal end 20B is at or near a target site at a proximal side of thrombus 96, the clinician may introduce mechanical cutter 18, including distal element 94, through inner lumen 40 of catheter 20, while mechanical cutter 18 and/or distal element 94 are in a reduced-profile delivery configuration. The clinician may distally advance support structure 66 of mechanical cutter 18 until distal element 94 passes distally through or distally past thrombus 96 and distal element 94 becomes located at a position that is distal to all or part of thrombus 96. The clinician may then actuate an appropriate mechanism (e.g., a pull wire, etc.) to expand distal element 94 from the delivery configuration to the deployed configuration depicted in FIG. 7. The clinician may then apply a proximal force, such as to support structure 66, to bring proximal-facing surface 100 into contact with a distal side of thrombus 96, thereby compressing thrombus distally against distal-most end 20B of catheter 20 and the area surrounding distal mouth 24.

As described above, the clinician may further actuate aspiration, such as a vacuum force or suction force, to further proximally withdraw at least a proximal portion 102 of thrombus 96 into distal mouth 24. Distal element 94 and/or the aspiration force, alone or in combination, may cause proximal portion 102 of thrombus 96 to come into contact with bristles 68 (or an equivalent structure) of mechanical cutter 18, thereby segmenting proximal portion 102 of thrombus 96. In some examples described herein, the proximal compression from distal element 94 against distal mouth 24 may cause thrombus 96 to form a fluid-tight seal over distal mouth 24, thereby enhancing the suction effect of the aspiration force, proximally withdrawing thrombus 96 farther into inner lumen 40 of catheter 20.

The clinician may distally advance expandable member 36 and/or proximally withdraw distal element 94 such that a majority of thrombus 96 comes into contact with, and is segmented by, bristles 68 of mechanical cutter 18. The segmented portions of thrombus 96 may be aspirated proximally through inner lumen 40 of catheter 20 and into a waste reservoir (not shown) via the suction force. The clinician may then proximally withdraw catheter 20, including mechanical cutter 18, from the vasculature of the patient.

Figure 8:
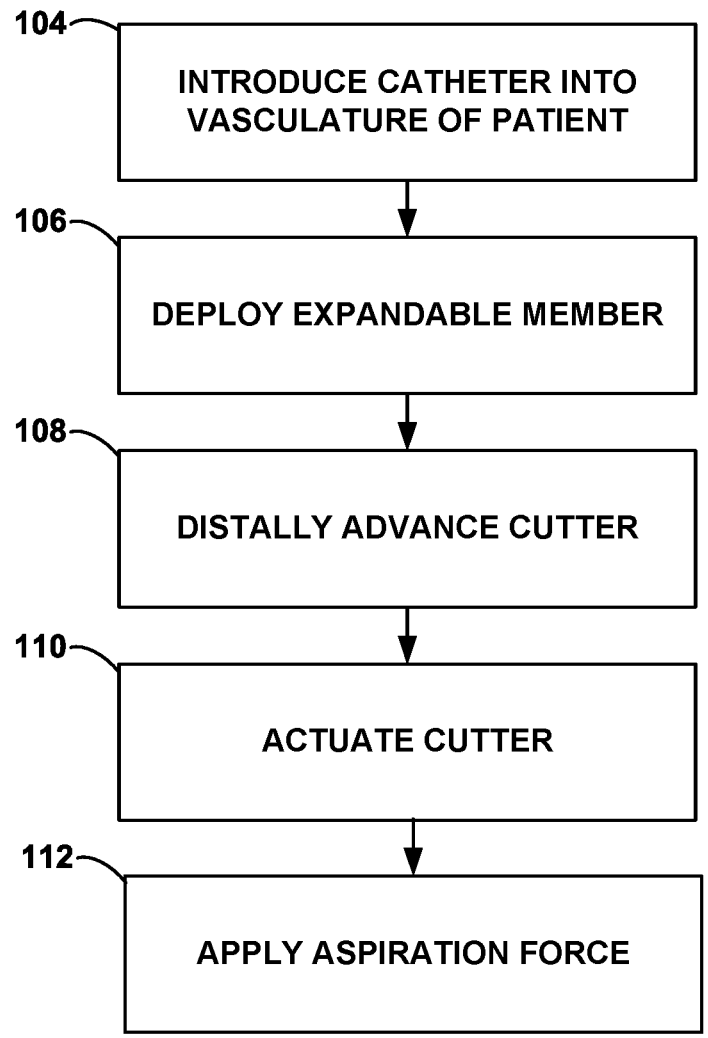
FIG. 8 is a flow diagram of an example method of using a catheter.

FIG. 8 is a flow diagram of an example method of using catheter 20 of FIGS. 2A and 2B. The techniques of FIG. 8 include inserting catheter 20 into vasculature of the patient (104), deploying expandable member 36 to expand expandable member 36 in the vasculature of the patient (106), distally advancing mechanical cutter 18 through catheter 20 (108), actuating mechanical cutter 18 (110), and aspirating a thrombus (112). In some examples, the techniques described herein include removing catheter 20 from the vasculature of the patient once the procedure is complete.

In some examples, inserting catheter 20 into vasculature of a patient (104) may include initially introducing a guidewire, guide catheter, or another guide member into the vasculature of the patient to a target treatment site. Elongated body 22 may then be introduced over the guidewire and advanced to the target treatment site. Additionally, or alternatively, catheter 20 may be introduced into vasculature of a patient with the aid of a guide catheter. For example, the guide catheter may be initially introduced into vasculature of a patient and positioned adjacent a target treatment site. Catheter 20 may then be introduced through an inner lumen of the guide catheter.

Once within the vasculature, expandable member 36 may be deployed into the vasculature (106). In some examples, expandable member 36 may be self-expanding and may expand without the aid of any additional expansion mechanisms once released from an outer introducer sheath. Additionally, or alternatively, expandable member 36 may be expanded using a balloon or pull wire. In other examples, expandable member may be expanded by applying electrical energy to expandable member 36. For example, expandable member 36 (or a portion or layer thereof) may be constructed using a shape memory alloy actuator material.

The technique of FIG. 8 also includes distally advancing mechanical cutter 18 through inner lumen 40 of catheter 20 (108). In some examples, catheter 20 includes a stopper element 78 (FIGS. 4-6) configured to control a relative longitudinal position of mechanical cutter 18 within lumen 40 of catheter 20. For instance, stopper element 78 may act as a distal stop that prevents a distal end or distal portion of mechanical cutter 18 from extending distally outward from distal mouth 24 of expandable member 36 and into direct engagement with a blood vessel wall. As another example, stopper element 78 may control the extent to which the distal end or distal portion of mechanical cutter 18 extends distally into inner lumen 40C of expandable member 36 from inner lumen 40B of elongated body 22 of catheter 20. In some examples, but not all examples, the clinician may expand mechanical cutter 18 from a delivery configuration to a deployed configuration once mechanical cutter 18 is at the desired longitudinal position.

The technique of FIG. 8 also includes actuating mechanical cutter 18 (110). For instance, the clinician may actuate a user-input mechanism to initiate a rotational motion, a longitudinal motion, or both, of mechanical cutter 18.

The technique of FIG. 8 also includes applying a suction force to inner lumen 40 of catheter 20 to proximally withdraw a thrombus into distal mouth 24 of catheter 20 (112). For example, once distal portion 32 of catheter 20 is positioned proximate to a thrombus, a clinician may actuate a suction source to apply a suction force to lumen 40. The suction source can comprise a pump, such as a direct-acting pump (e.g., a peristaltic pump, or a lobe, vane, gear, or piston pump, or other suitable pumps of this type) or an indirect-acting pump (e.g., a vacuum pump, which creates a partial vacuum in an evacuation volume fluidically coupled to the liquid to be displaced). In some examples, the suction force applied to inner lumen 40 of catheter 20 is varied over time, referring to herein as cyclical aspiration. As discussed above, during this cyclical aspiration, at least a portion of the thrombus may be pulled into contact with actuated mechanical cutter 18, thereby segmenting the thrombus into smaller pieces, which are then aspirated proximally through inner lumen 40 of catheter 20. Catheter 20 may be removed from the vasculature once the aspiration procedure is complete.

Various aspects of the disclosure have been described. These and other aspects are within the scope of the following claims.

What is claimed is:
1. A medical device comprising:
an elongated body comprising an expandable member disposed at a distal portion of the elongated body, the elongated body further comprising an interior surface defining an inner lumen, wherein the expandable mem- ber defines an expandable distal mouth of the elongated body, the expandable distal mouth being open to the inner lumen;

a rotatable cutting tool located within the inner lumen of the elongated body, the rotatable cutting tool configured to segment a thrombus into smaller pieces while an aspiration force pulls the thrombus proximally into the inner lumen;

an intermediate structure oriented radially between the rotatable cutting tool and the interior surface of the elongated body, the intermediate structure configured to prevent the cutting tool from contacting the interior surface of the elongated body, wherein the intermediate structure is configured to move longitudinally through the inner lumen; and a stopper configured to limit movement of the cutting tool distally past a distal end of the expandable member, wherein the stopper is configured to engage with a lip extending radially inward from the interior surface of the elongated body.

2. The medical device of claim 1, wherein the intermediate structure is configured to retain the cutting tool in an approximately radially central position within the inner lumen.

3. The medical device of claim 1, wherein the cutting tool is configured to expand radially outward from a delivery configuration to a deployed configuration, and wherein the cutting tool is configured to rotate within a volume defined by the inner lumen.

4. The medical device of claim 1, wherein the cutting tool comprises a brush including a plurality of bristles extending radially outward from an elongated support member.

5. The medical device of claim 4, wherein the brush tapers radially inwardly as it extends in a distal direction.

6. The medical device of claim 1, wherein the intermediate structure comprises a sheath that radially surrounds the cutting tool.

7. The medical device of claim 1, wherein the stopper comprises a silicone plug disposed on the cutting tool.

8. The medical device of claim 1, wherein the stopper comprises a fluid-expandable balloon.

9. The medical device of claim 1, further comprising a distal member configured to apply a proximal force onto a distal side of the thrombus to push the thrombus into the expandable member.

10. The medical device of claim 1, wherein the elongated body comprises a catheter.

11. A system comprising:
the medical device of claim 1; and
an aspiration source configured to generate the aspiration force of claim 1.

12. The system of claim 11, further comprising control circuitry configured to control a rotation of the cutting tool and configured to control the aspiration source to vary the aspiration force.

13. A method comprising using a medical device to segment a thrombus, wherein the medical device comprises:
an elongated body comprising an expandable member disposed at a distal portion of the elongated body, the elongated body further comprising an interior surface defining an inner lumen, wherein the expandable member defines an expandable distal mouth of the elongated body, the expandable distal mouth being open to the inner lumen;

a rotatable cutting tool located within the inner lumen of the elongated body, the rotatable cutting tool configured to segment the thrombus into smaller pieces while an aspiration force pulls the thrombus proximally into the inner lumen;

an intermediate structure oriented radially between the rotatable cutting tool and the interior surface of the elongated body, the intermediate structure configured to prevent the cutting tool from contacting the interior surface of the elongated body, wherein the intermediate structure is configured to move longitudinally through the inner lumen; and a stopper configured to limit movement of the cutting tool distally past a distal end of the expandable member, wherein the stopper is configured to engage with a lip extending radially inward from the interior surface of the elongated body.

14. The method of claim 13, wherein using the medical device to segment the thrombus comprises:
navigating the elongated body to a target site within vasculature of a patient;
distally inserting the cutting tool into the inner lumen of the elongated body and into the expandable member;
deploying the cutting tool from a delivery configuration to a deployed configuration; and
actuating a rotation of the cutting tool to segment the thrombus.

15. The method of claim 14, wherein using the medical device to segment the thrombus further comprises:
positioning a distal member on a distal side of the thrombus; and
proximally withdrawing the distal member to push the thrombus into the expandable member.

16. A medical device comprising:
an elongated body defining an inner lumen and comprising an expandable member disposed at a distal portion of the elongated body, wherein the expandable member defines an expandable distal mouth of the elongated body, the expandable distal mouth being open to the inner lumen;

a rotatable cutting tool located within the inner lumen of the elongated body, the rotatable cutting tool configured to segment a thrombus into smaller pieces while an aspiration force pulls the thrombus proximally into the inner lumen; and a stopper configured to limit movement of the cutting tool distally past a distal end of the expandable member, wherein the stopper is configured to engage with a lip extending radially inward from an interior surface of the elongated body; and an intermediate structure oriented radially between the rotatable cutting tool and the interior surface of the elongated body, the intermediate structure configured to prevent the cutting tool from contacting the interior surface of the elongated body and to retain the cutting tool in an approximately radially central position within the inner lumen.

17. The medical device of claim 16, wherein the intermediate structure comprises a sheath that radially surrounds the cutting tool.

18. The medical device of claim 16, further comprising a distal member configured to apply a proximal force onto a distal side of the thrombus to push the thrombus into the expandable member.

* * * * *